United States Patent
Chassard et al.

(10) Patent No.: US 11,179,427 B2
(45) Date of Patent: Nov. 23, 2021

(54) BABY FOOD COMPOSITION COMPRISING VIABLE PROPIONIC ACID-PRODUCING BACTERIA

(71) Applicants: ETH ZURICH, Zürich (CH); UNIVERSITÄT ZÜRICH, Zürich (CH)

(72) Inventors: Christophe Chassard, Lempdes (FR); Christophe Lacroix, Kilchberg (CH); Christian Braegger, Zürich (CH); Vanesa Natalin Rocha Martin, Zürich (CH)

(73) Assignee: ETH ZURICH, Zürich (CH)

( * ) Notice: Subject to any disclaimer, the term of this patent is extended or adjusted under 35 U.S.C. 154(b) by 420 days.

(21) Appl. No.: 16/251,351

(22) Filed: Jan. 18, 2019

(65) Prior Publication Data

US 2019/0183944 A1    Jun. 20, 2019

Related U.S. Application Data

(63) Continuation-in-part of application No. 14/761,336, filed as application No. PCT/CH2014/000006 on Jan. 14, 2014, now abandoned.

(30) Foreign Application Priority Data

Jan. 21, 2013 (EP) .................... 13000283

(51) Int. Cl.
A61K 35/744 (2015.01)
A61K 35/747 (2015.01)
(Continued)

(52) U.S. Cl.
CPC .......... *A61K 35/747* (2013.01); *A23L 33/135* (2016.08); *A23L 33/40* (2016.08);
(Continued)

(58) Field of Classification Search
CPC .................................................... A61K 35/744
See application file for complete search history.

(56) References Cited

U.S. PATENT DOCUMENTS 5,599,795 A    2/1997 McCann et al.
6,080,401 A    6/2000 Reddy et al.
(Continued)

FOREIGN PATENT DOCUMENTS

EP    0 433 299 B1    5/1998
EP    1 308 506 A1    5/2003
(Continued)

OTHER PUBLICATIONS

International Search Report for corresponding International Application No. PCT/CH2014/000006 dated Mar. 27, 2014.
(Continued)

*Primary Examiner* — Rosanne Kosson
(74) *Attorney, Agent, or Firm* — Renner, Otto, Boisselle & Sklar, LLP

(57) ABSTRACT

The present invention relates to compositions, particularly baby food compositions, including living propionic acid-producing bacteria, preferably lactate-utilizing propionic acid-producing bacteria, their manufacture and use in the treatment of digestive diseases, particularly for treatment of infantile colic.

12 Claims, 12 Drawing Sheets

(51) Int. Cl.
  *A61K 9/00*       (2006.01)
  *A61K 35/745*     (2015.01)
  *A61P 1/06*       (2006.01)
  *A23L 33/135*     (2016.01)
  *A23L 33/00*      (2016.01)

(52) U.S. Cl.
  CPC .......... *A61K 9/0095* (2013.01); *A61K 35/745* (2013.01); *A61P 1/06* (2018.01); *A23V 2002/00* (2013.01)

(56) References Cited

U.S. PATENT DOCUMENTS

| | | |
|---|---|---|
| 6,262,019 B1 | 7/2001 | Keller et al. |
| 6,645,530 B1 | 11/2003 | Borody |
| RE39,705 E | 6/2007 | Keller et al. |
| 7,374,924 B2 | 5/2008 | Connolly et al. |
| RE40,849 E | 7/2009 | Keller et al. |
| 7,629,155 B2 | 12/2009 | Sato et al. |
| 7,834,061 B2 | 11/2010 | Sato et al. |
| 8,025,911 B2 | 9/2011 | Uchida et al. |
| 8,110,607 B2 | 2/2012 | Sato et al. |
| 8,241,684 B2 | 8/2012 | Uchida et al. |
| 8,309,073 B2 | 11/2012 | Mayra-Makinen et al. |
| 8,460,648 B2 | 6/2013 | Borody |
| 8,604,005 B2 | 12/2013 | Kajander et al. |
| 8,691,213 B2 | 4/2014 | Langford et al. |
| 8,758,842 B2 | 6/2014 | Furuichi et al. |
| 9,040,036 B2 | 5/2015 | Borody |
| 9,050,358 B2 | 6/2015 | Borody |
| 9,057,112 B2 | 6/2015 | Connolly et al. |
| 9,255,246 B2 | 2/2016 | Scatizzi |
| 9,320,763 B2 | 4/2016 | Borody |
| 2003/0138476 A1 | 7/2003 | Van Leeuwen et al. |
| 2004/0062757 A1 | 4/2004 | Finegold |
| 2004/0062758 A1 | 4/2004 | Mayra-Makinen et al. |
| 2004/0005304 A1 | 6/2004 | Brudnak |
| 2004/0170617 A1 | 9/2004 | Finegold |
| 2004/0185032 A1 | 9/2004 | Burrell |
| 2005/0180963 A1 | 8/2005 | Adams et al. |
| 2007/0258953 A1 | 11/2007 | Duncan et al. |
| 2007/0298013 A1 | 12/2007 | Altman |
| 2008/0069861 A1 | 3/2008 | Brown et al. |
| 2008/0311097 A1 | 12/2008 | Israelsen |
| 2010/0028449 A1 | 2/2010 | Prakash et al. |
| 2010/0166721 A1 | 7/2010 | Masri |
| 2010/0284979 A1 | 11/2010 | O'Mahoney et al. |
| 2011/0052538 A1 | 3/2011 | Brown et al. |
| 2011/0110905 A1 | 5/2011 | Ritchie |
| 2011/0165127 A1 | 7/2011 | Masri |
| 2011/0189132 A1 | 8/2011 | Garner et al. |
| 2011/0223137 A1 | 9/2011 | Darmaun et al. |
| 2012/0034198 A1 | 2/2012 | Garner et al. |
| 2012/0121562 A1 | 5/2012 | Bergonzelli Degonda et al. |
| 2012/0121564 A1 | 5/2012 | Connolly et al. |
| 2012/0128726 A1 | 5/2012 | Mercenier et al. |
| 2012/0134973 A1 | 5/2012 | Kekkonen |
| 2012/0171166 A1 | 7/2012 | Chow et al. |
| 2012/0230956 A1 | 9/2012 | McLean et al. |
| 2012/0269789 A1 | 10/2012 | Mercenier et al. |
| 2013/0189236 A1 | 7/2013 | Ware |
| 2013/0224166 A1 | 8/2013 | Mercenier et al. |
| 2013/0273015 A1 | 10/2013 | Klassen et al. |
| 2013/0280239 A1 | 10/2013 | Klassen et al. |
| 2013/0330307 A1 | 12/2013 | Millan |
| 2013/0330308 A1 | 12/2013 | Millan et al. |
| 2014/0037603 A1 | 2/2014 | Bolster et al. |
| 2014/0093479 A1 | 4/2014 | Mogna et al. |
| 2014/0112985 A1 | 4/2014 | Bochenek et al. |
| 2014/0193542 A1 | 7/2014 | Langford et al. |
| 2014/0234279 A1 | 8/2014 | Millan |
| 2015/0174080 A1 | 6/2015 | Schiffrin et al. |
| 2015/0181916 A1 | 7/2015 | Klassen et al. |
| 2015/0290261 A1 | 10/2015 | Chichlowski et al. |
| 2015/0352162 A1 | 12/2015 | Chassard et al. |

FOREIGN PATENT DOCUMENTS

| | | | |
|---|---|---|---|
| EP | 1 374 878 A1 | 1/2004 | |
| EP | 0 888 118 B1 | 11/2004 | |
| EP | 1 987 835 A2 | 11/2008 | |
| EP | 1 513 541 B1 | 1/2009 | |
| EP | 1 782 818 B1 | 9/2009 | |
| EP | 1 869 161 B1 | 1/2010 | |
| EP | 2 110 133 B1 | 8/2011 | |
| EP | 1 531 841 B1 | 11/2011 | |
| EP | 2 169 050 B1 | 4/2014 | |
| EP | 2 585 085 B1 | 5/2014 | |
| EP | 2 164 349 B1 | 9/2014 | |
| EP | 2 040 722 B1 | 11/2015 | |
| WO | 2004000340 A2 | 12/2003 | |
| WO | 2004085628 A1 | 10/2004 | |
| WO | 2005060937 A1 | 7/2005 | |
| WO | 2011020780 A1 | 2/2011 | |
| WO | 2012059502 A1 | 5/2012 | |
| WO | 2012142605 A1 | 10/2012 | |
| WO | WO-2014110685 A1 * | 7/2014 | .......... A61K 35/741 |
| WO | 2015017625 A1 | 2/2015 | |
| WO | 2015018883 A2 | 2/2015 | |
| WO | 2015065194 A1 | 5/2015 | |
| WO | 2015112083 A1 | 7/2015 | |
| WO | 2015120098 A1 | 8/2015 | |
| WO | 2015177246 A2 | 11/2015 | |

OTHER PUBLICATIONS

Written Opinion for corresponding International Application No. PCT/CH2014/000006 dated Mar. 27, 2014.
O'Callaghan et al., "Infant Formulae—New Developments", Encyclopedia of Dairy Sciences, 2012, pp. 1384-1392 (cited in specification on p. 1).
Moat et al., "Fermentation Pathways",Microbial Physiology, Chapter 11, 2002, pp. 412-433 (cited in specification on p. 4).
Hosseini et al., "Propionate as a health-promoting microbial metabolite in the human gut", Nutrition Reviews, vol. 69 (5), 2011, pp. 245-258 (cited in specification on p. 8).
Arslanoglu et al., "Early Dietary Intervention with a Mixture of Prebiotic Oligosaccharides Reduces the Incidence of Allergic Manifestations and Infections during the First Two Years of Life", The Journal of Nutrition, Nutrition and Disease, 2008, pp. 1091-1095 (cited in specification on p. 9).
Grattepanche et al., "Production of viable probiotic cells", Microbial production of food ingredients, enzymes and nutraceuticals, 2013, pp. 321-352 (cited in specification on p. 15).
Walstra et al., "Milk Powder", Dairy Science and Technology, Chapter 20, 2006, pp. 513-535 (cited in specification on p. 15).
Schuck, "Dehydrated Dairy Products / Milk Powder: Types and Manufacture", Encyclopedia of Dairy Sciences, 2011, pp. 108-116 (cited in specification on p. 15).
Jay et al., Modern Food Microbiology, Seventh Edition, 2005, 45 pages (cited in specification on p. 7).
Braegger et al., "Supplementation of Infant Formula With Probiotics and/or Prebiotics: A Systematic Review and Comment by the ESPGHAN Committee on Nutrition", JPGN, vol. 52, No. 2, Feb. 2011.
Parker et al., "Interactions of Lactobacillus and Propionibacterium in Mixed Culture", Journal of Food Protection, vol. 45, No. 4, Mar. 1982, pp. 326-330.
Pham et al., "Lactate-utilizing community is associated with gut microbiota dysbiosis in colicky infants", Nature, Scientific Reports, 7:11176, Sep. 2017, pp. 1-13.
Rocha Martin et al., "Colonization of Cutibacterium avidum during infant gut microbiota establishment", FEMS Microbiology Ecology, No. 95, No. 1,2019, pp. 1-14.

* cited by examiner

| Taxon | Relative Abundance | | | | | | | | | | | | Reference |
|---|---|---|---|---|---|---|---|---|---|---|---|---|---|
| | Control Reactor | | | | Test Reactor 1 | | | | Test Reactor 4 | | | | |
| | A | B | C | D | A | B | C | D | A | B | C | D | |
| Bacteroides | | | | | | | | | | | | | 46% |
| Prevotella | | | | | | | | | | | | | 23% |
| Veillonella | | | | | | | | | | | | | 11% |
| Parabacteroides | | | | | | | | | | | | | 6% |
| Dialister | | | | | | | | | | | | | 3% |
| Coprococcus | | | | | | | | | | | | | 1% |
| Propionibacterium | | | | | | | | | | | | | 0% |
| Total abundance propionate-producing bacteria | 21.6% | 20.8% | 31.3% | 19.2% | 14.4% | 17.9% | 16.4% | 15.7% | 17.4% | 25.2% | 24.2% | 21.0% | |

Figure 3A

BABY FOOD COMPOSITION COMPRISING VIABLE PROPIONIC ACID-PRODUCING BACTERIA

PRIOR APPLICATION DATA

This application is a continuation-in-part of U.S. patent application Ser. No. 14/761,336 filed Jul. 16, 2015, which is a national phase of International Application No. PCT/CH2014/000006, filed Jan. 14, 2014, which claims priority to Application No. EP 13000283.5, filed Jan. 21, 2013.

TECHNICAL FIELD

The present invention relates to compositions, particularly baby food compositions, comprising viable propionic acid-producing bacteria, their manufacture and use in the treatment of digestive diseases, particularly for treatment of infantile colics (IC).

BACKGROUND

It is well known that human milk from healthy and well-nourished mothers provides adequate nutrition for infants during the first few months of life and also significantly reduces the risk of acute and chronic diseases during this critical development period. For infant nutritional products, the chemical composition of human milk served as a guide for the formulation of infant formula. In recent years, selected physiological outcomes have gained acceptance in documenting the functionality of novel ingredients, including some chemical entities not found in human milk.

Callaghan et al (Infant Formulae, in: Encyclopedia of Dairy Sciences (2nd Ed), Editor: John W. Fuquay, Elsevier Ltd, pp 135-145, incorporated by reference) summarizes regulations governing the manufacture, composition, and labeling of infant nutritional products. These regulations ensure safety and efficiency of the products but also provide limitations for new nutritional products.

A number of infant nutritional products, comprising probiotics, are commercially available. These products involve selected lactate-producers (either *Bifidobacterium* or *Lactobacillus*): Nestle Good Start® supplemented with *Bifidobacterium lactis*; Lactogen 3® supplemented with *Lactobacillus reuteri*; Guigoz Croissance 3® supplemented with *Lactobacillus reuteri*.

Further, a number of documents relate to nutritional products comprising bacteria and having a therapeutic use.

WO2004/085628 describes lactic acid utilizing bacteria and their therapeutic use, particularly for treatment of inflammatory diseases.

WO2011/020780 describes nutritional compositions comprising lactococcus strains and their therapeutic use, particularly for the treatment of allergy symptoms.

US2010/0166721 describes probiotic compositions and in very general terms its use as a food supplement for normalization of the gastrointestinal flora.

EP1374878 describes methods and compositions for preventing or alleviating symptoms of malabsorption from the GI tract.

US2004/0062758 describes a combination of probiotics and its use for stimulating the immune system and for general health improvement.

WO2012/059502 describes a powdered cereal based composition comprising probiotic micro-organisms and its use in strengthening the immune system or treatment of inflammatory disorders. The document is specifically directed to non-replicating micro-organisms.

US2012/0171166 describes symbiotic combination of specific oligosaccharides to promote growth of beneficial microbiota and its use for treating GI disorders. The document is specifically directed to butyrate producing bacteria.

US2007/0258953 describes probiotic compositions comprising viable, novel lactic acid utilizing bacteria; as well as their use as a medicament.

US2005/0180963 describes probiotic compositions comprising viable, novel propionibacteria; as well as their use in the treatment of GI diseases.

None of the above documents address the treatment of digestive diseases or disorders selected from the group consisting of colics, intestinal discomfort, intestinal pain, visceral sensitivity and intestinal cramp, particularly the treatment of infantile colics. Even more, it is believed there is no established treatment of infantile colics known today. In consequence, there is an unmet clinical need.

SUMMARY

The present invention addresses this clinical need and overcomes at least some of these drawbacks of the state of the art. In particular, the present invention to provides food/pharmaceutical compositions for treatment of digestive diseases, such as infantile colics (IC) as well as methods for treatment of the above disorders. These results are achieved by the composition as described in the present disclosure.

Accordingly, in a first aspect, a method of treating infantile colic is provided. The method includes administering to a patient an infant nutritional product including (a) viable lactic acid-producing bacteria from one or more live bacteria strains; (b) viable, lactate utilizing, propionic acid producing bacteria from one or more live Cutibacteria strains, and (c) optionally prebiotics.

In an embodiment, said viable lactate utilizing, propionic acid producing bacteria are *C. avidum*.

In an embodiment, said viable lactic acid-producing bacteria (a) are selected from the group of Lactic Acid Bacteria and *Bifidobacteria*.

In another embodiment, said viable lactic acid-producing bacteria (a) are selected from *Bifidobacteria* and relatives, *Lactobacilli* and relatives, *Lactococci* and relatives, *Streptococci* and relatives, *Enterococci* and relatives, *Leuconostoc* and relatives, *Weissella* and relatives.

In another embodiment, the infant nutritional product further comprises additives and/or growth enhancing supplements and/or prebiotics.

In another embodiment, the infant nutritional product includes prebiotics, and the prebiotics are selected from the group consisting of FOS and GOS.

In another embodiment, the infant nutritional product further comprises baby milk or baby milk powder.

In another embodiment, the amount of said viable bacteria is in the range of $10^2$ to $10^{12}$ CFU per gram or per mL of product.

In another embodiment, the infant nutritional product is designed to be administered to infants or young children starting from the age of 6 months and provides complete nutrition to the infant or child.

In another embodiment, the method includes administering a baby formula comprising the infant nutritional product.

In another embodiment, the baby formula is in the form of a baby milk.

In another embodiment, the baby formula is in the form of a kit of parts, wherein a first part comprises the infant nutritional product and the second part comprises a baby formula free of viable bacteria.

In another embodiment, the second part comprises baby milk.

BRIEF DESCRIPTION OF THE DRAWINGS

FIG. 3A is a heat-map showing the relative abundance at genus level of potential propionate producers, according to Example 1 described herein.

DETAILED DESCRIPTION

Figure 1:
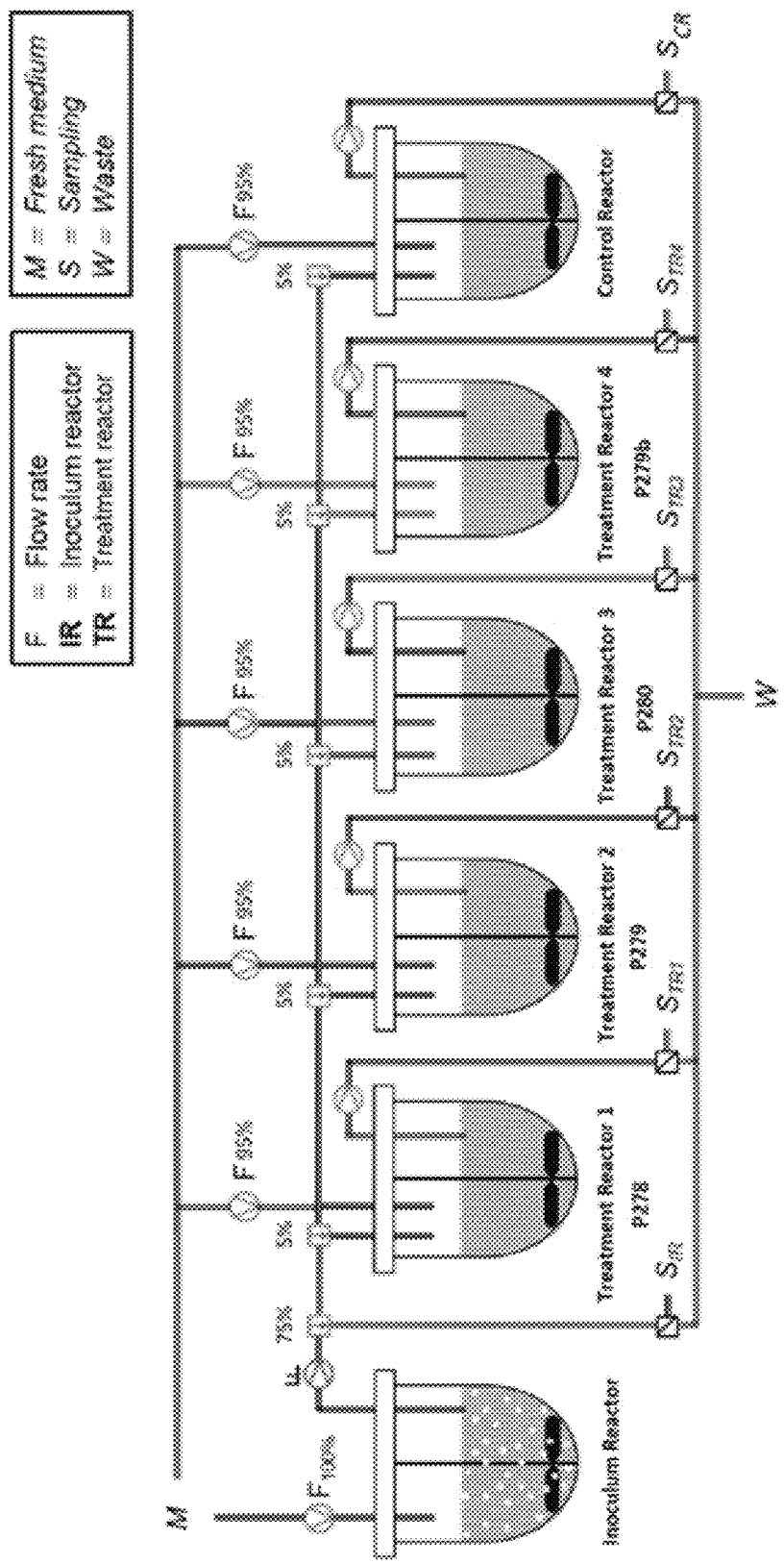
FIG. 1 is a schematic diagram illustrating a two-stage fermentation reactor system, as used in Example 1 described herein.

The present invention will be described in more detail below. It is understood that the various embodiments, preferences and ranges as provided/disclosed in this specification may be combined at will. Further, depending of the specific embodiment, selected definitions, embodiments or ranges may not apply.

Unless otherwise stated, the following definitions shall apply in this specification:

As used herein, the term "a," "an,", "the" and similar terms used in the context of the present invention (especially in the context of the claims) are to be construed to cover both the singular and plural unless otherwise indicated herein or clearly contradicted by the context.

As used herein, the terms "including", "containing" and "comprising" are used herein in their open, non-limiting sense.

The term "treatment" shall also include the delay of progression as well as the prevention (prophylaxis).

The terms "digestive diseases" and "digestive disorders" are well known and describe diseases/disorders that pertain to the gastrointestinal tract, particularly the gut. Particularly included are infantile colics ("IC"). Diagnostic criteria for IC must include all of the following in infants from birth to 4 months of age: 1. Paroxysms of irritability, fussing or crying that starts and stops without obvious cause; 2. Episodes lasting 3 or more hours/day and occurring at least 3 days/week for at least 1 week; 3. No failure to thrive. IC is also known as baby colic, ICD-10: R10.4.

The term "propionic acid-producing bacteria" refers to a group of bacteria that produce propionate as main product from the carbon metabolism.

The term "propionic acid bacteria" refers to bacteria having unique metabolism leading to propionic acid as a major end product of metabolism. Such bacteria may ferment a large number of substrates, including lactate. The major end products of propionic fermentation are propionic, acetic, and succinic acids and $CO_2$. Sugar substrates (glucose mainly) are first oxidized to pyruvate via glycolysis or via the pentose phosphate pathway, generating ATP and reduced coenzymes. Pyruvate is further catabolized via two main pathways, producing either propionate or acetate and $CO_2$. Lactate can be metabolized to propionate by the acrylate pathway where water is removed from lactate to form acrylate with subsequent reduction to propionate (Microbial Physiology. Albert G. Moat, John W. Foster and Michael P. Spector, Wiley-Liss, Inc.

Propionic acid bacteria have a generally recognized as safe status (GRAS) in the United States and a qualified presumption of safety (QPS) status in Europe.

Propionic acid bacteria are classified in the class of Actinobacteria with other Gram-positive bacteria with a GC content higher than 50%.

The terms "Lactate-utilizing, propionic acid-producing bacteria" and "lactic acid producing bacteria" are defined below.

The term "probiotics" is well known and established in the field and particularly relates to microbial cell preparations or components of microbial cells that have a beneficial effect on the health and well-being of humans. Accordingly, the term probiotics encompasses the above defined bacteria.

The term "prebiotic" is well known and established in the field and particularly relates to a non-digestible food ingredient that beneficially affects humans by selectively stimulating the growth and/or activity of one or a limited number of bacteria in the colon, and thus improves human health.

In more general terms, in a first aspect, the invention relates to new compositions comprising viable propionic acid-producing bacteria, preferably viable lactate-utilizing, propionic acid-producing bacteria. These inventive compositions may be adapted to food compositions, particularly baby food compositions, and/or pharmaceutical compositions. This aspect of the invention shall be explained in further detail below:

Food composition: The inventive compositions may be in the form of any food composition. Preferably, the compositions are adapted to infant, particularly baby, nutrition in the form of an infant nutritional product. Accordingly, the food composition may be in the form of an infant starter formula, a follow-on formula, a baby food formula, an infant cereal formula or a growing-up milk. Such food compositions are known and described e.g. in Callaghan et al (Infant Formulae, in: Encyclopedia of Dairy Sciences ($2^{nd}$ Ed), Editor: John W. Fuquay, Elsevier Ltd, pp 135-145, incorporated by reference)). Typically, such food compositions comprise additives and growth enhancing elements as described below. The term food composition also encompasses an adult nutritional composition, or an adult milk-protein based drink for individuals in need of therapy. Preferably, said food composition is a starter infant formula, such as a baby milk or baby milk powder.

Pharmaceutical compositions: The inventive compositions may be in the form of any pharmaceutical formulation, such as solid, semi-solid or liquid formulation. Further, the above food compositions may also be used as a pharmaceutical composition. Pharmaceutical compositions comprise, next to the composition to be administered, also instructions for the administration ("package insert").

Viable (living) bacteria: The use of viable (living) bacteria is believed to be a key feature of the present invention, distinguishing it from the prior art and allowing the uses described herein. According to the invention, the bacteria are viable (living), i.e. they are metabolically active and/or are able to colonize the gut of a mammalian, particularly a human. The term includes both (i) bacteria able to divide and form a colony and (ii) bacteria which are non-replicating. Bacteria of group (i) are able to divide and form a colony on a nutrient medium appropriate for the growth of the bacteria, or to increase turbidity of liquid growth medium after inoculation with different concentrations of bacterial preparations and incubation under appropriate conditions (aerobic and/or anaerobic atmosphere for at least 24 h). Such classical plating methods are known and described e.g. in Jay et al (Modern Food Microbiology. 7th Edition, Springer, 2005). Bacteria of group (ii) includes live but non-replicating bacteria that can be enumerated with fluorescent stains targeting bacterial membrane potentials or enzymatic activities enabled the differentiation between viable, metabolic active, damaged, dormant, viable but not cultivable, and dead bacterial cells. Molecular tools like fluorescence in situ hybridization (FISH) and flow cytometry were successfully applied to estimate viable cells in probiotic products.

In a preferred embodiment, the invention relates to compositions comprising bacteria of group (i).

In an alternative embodiment, the invention relates to compositions additionally comprising bacteria of group (ii).

In an alternative embodiment, the invention relates to compositions only comprising bacteria of group (ii).

The amount of such bacteria may vary over a broad range and an effective amount may be determined by the skilled person in routine experiments. Amounts effective for this purpose will depend on a number of factors known to those of skill in the art such as the weight and general health state of the human to be treated, and on the effect of the food matrix. Typically, the effective amount in the compositions of the present invention is in the range of $10^2$ to $10^{12}$ cfu/g, more preferably $10^4$ to $10^9$ cfu/g, most preferably $10^7$ to $10^9$ cfu/g composition or per mL of composition.

Lactate-utilizing, propionic acid-producing bacteria: In a preferred embodiment, the propionic acid-producing bacteria are selected from the group of "Lactate utilizing propionic acid-producing bacteria". Gut bacteria utilizing lactate to produce propionate though the acrylate pathways include Propionibacteria and relatives, Veillonella and relatives, Selomonas and relatives, Megasphaera and relatives, Cutibacteria and relatives and any other lactate utilizing propionate producing bacteria isolated from the infant intestinal ecosystem. The acrylate pathway is known and described in literature, e.g. Hosseini et al. (Nutr. Rev. 9:245-258, 2011), particularly FIG. 2, which is incorporated by reference in its entirety.

In a further preferred embodiment, the propionic acid-producing bacteria are selected from the currently known 13 species.

In a further preferred embodiment, the propionic acid-producing bacteria are selected from the group of *P. freudenreichii, P. acidipropionici, P. jensenii, P. thoenii, P. cyclohexanicum, P. microaerophilum* and *C. avidum*.

Accordingly, the invention provides for a composition, particularly a food composition or a pharmaceutical composition, comprising (i) viable propionic acid-producing bacteria from one or more live bacteria strains, particularly from strains as identified herein; (ii) optionally a source of proteins, (iii) optionally a source of carbohydrates, (iv) optionally a source of lipids; (v) optionally a source of vitamins and minerals; (vi) optionally additives; (vii) optionally water.

The composition according to the present invention typically contains a protein source. Suitable are amounts of not more than 2.0 g/IOO kcal, preferably 1.8 to 2.0 g/100 kcal. The type of protein is not believed to be critical to the present invention provided that the minimum requirements for essential amino acid content are met and satisfactory growth is ensured although it is preferred that over 50% by weight of the protein source is whey. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in whatever proportions are desired.

The composition according to the present invention typically contains a carbohydrate source. Any carbohydrate source conventionally found in infant formulae such as lactose, saccharose, maltodextrin, starch and mixtures thereof may be used although the preferred source of carbohydrates is lactose. Preferably the carbohydrate sources contribute between 35 and 65% of the total energy of the composition.

The composition according to the present invention typically contains a source of lipids. The lipid source may be any lipid or fat which is suitable for use in infant formulas. Preferred fat sources include palm olein, high oleic sunflower oil and high oleic safflower oil. The essential fatty acids linoleic and [alpha]-linolenic acid may also be added as may small amounts of oils containing high quantities of preformed arachidonic acid and docosahexaenoic acid such as fish oils or microbial oils. In total, the fat content is preferably such as to contribute between 30 to 55% of the total energy of the formula. The fat source preferably has a ratio of n-6 to n-3 fatty acids of about 5:1 to about 15:1; for example, about 8:1 to about 10:1.

The composition according to the invention typically contains all vitamins and minerals understood to be essential in the daily diet and in nutritionally significant amounts. Minimum requirements have been established for certain vitamins and minerals. Examples of minerals, vitamins and other nutrients optionally present in the infant formula include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chloride, potassium, sodium, selenium, chromium, molybdenum, taurine, and L-carnitine. Minerals are usually added in salt form. The presence and amounts of specific minerals and other vitamins will vary depending on the intended infant population.

The composition according to the invention may be dry. This ensures a stable composition comprising living bacteria as defined herein. However, low water content, typically below 5%, may be acceptable and is thus comprised within the present invention.

The composition according to the invention may further contain other components which may have a beneficial effect such as fibers, lactoferrin, nucleotides, nucleosides, and the like.

The composition according to the invention may further contain emulsifiers and stabilizers such as soy lecithin, citric acid esters of mono- and di-glycerides, and the like. This is especially the case if the composition is provided in liquid form.

The composition according to the invention may further contain stabilizers (or "stabilizing agents"). This term refers to compounds or materials that are added to the composition to increase the viscosity of the wet formulation or to form a hydrogel. Examples of a suitable stabilizer agent include but are not limited to polysaccharides, such as, cellulose acetate phthalate (CAP), carboxy-methyl-cellulose, pectin, sodium alginate, salts of alginic acid, hydroxyl propyl methyl cellulose (HPMC), methyl cellulose, carrageenan, guar gum, gum acacia, xanthan gum, locust bean gum, chitosan and chitosan derivatives, collagen, polyglycolic acid, starches and modified starches, cyclodextrins and oligosaccharides (inulin, maltodextrins, raffinose, dextrans, etc.) and combinations thereof.

The composition according to the invention may further contain protecting agents (or "protective agents" or "protectants"). This term refers to compounds or materials that are added to ensure or increase the stability of the viable bacteria during the drying process and afterwards, or for long-term storage stability of the dry powder product. Suitable protectants are generally readily soluble in a solution and do not thicken or polymerize upon contact with water. Suitable protectants are described below and include, but are not limited to, proteins such as human and bovine serum albumin, whey protein, soy protein, caseinate, gelatin, immunoglobulins, carbohydrates including monosaccharides (galactose, D-mannose, sorbose, etc.), disaccharides (lactose, trehalose, sucrose, etc.), an amino acid such as monosodium glutamate, lysine, glycine, alanine, arginine or histidine, as well as hydrophobic amino acids (tryptophan, tyrosine, leucine, phenylalanine, etc.); a methylamine such as betaine; an excipient salt such as magnesium sulfate; a polyol such as trihydric or higher sugar alcohols (e.g., glycerin, erythritol, glycerol, arabitol, xylitol, sorbitol, and mannitol); propylene glycol; polyethylene glycol; pluronics; surfactants, and combinations thereof.

The composition according to the invention may further contain prebiotic additives. This term refers to compounds/materials used to stimulate the growth of specific gut microbes, such as the viable bacteria as defined herein. Suitable prebiotics are known to the skilled person and are non-digestible food ingredients that beneficially affect the host by selectively stimulating the growth and/or activity of one or a limited number of bacteria in the colon. Such ingredients are non-digestible in the sense that they are not broken down and absorbed in the stomach or small intestine and thus pass intact to the colon where they are selectively fermented by the beneficial bacteria. Examples of suitable prebiotics include certain oligosaccharides, such as fructooligosaccharides (FOS), acacia gum and galactooligosaccharides (GOS). A combination of prebiotics may be used such as short chain GOS with long chain FOS such as the product sold under the trade mark Immunofortis® (Arslanoglu S. et al. J Nutr 2008; 138: 1091-5).

In a preferred embodiment, the invention provides a composition comprising a combination of viable bacteria as defined herein and prebiotics as defined herein. A combination of both components significantly improves the therapeutic and/or prophylactic effects as described herein (synergism).

In a further preferred embodiment, the invention provides a composition comprising a combination of viable bacteria, as defined herein, and lactic acid-producing bacteria. Preferably, the lactic acid-producing bacteria are selected from the group consisting of Lactic Acid Bacteria and Bifidobacteria. Preferably, lactic acid producing bacteria are selected from the strains consisting of *Bifidobacteria* and relatives thereof, Lactobacilli and relatives thereof, Lactococci and relatives thereof, *Steptococci* and relatives thereof, *Enterococci* and relatives thereof, *Leuconostoc* and relatives thereof, and *Weissella* and relatives thereof. It was found that the combination of lactic acid-producing bacteria and lactate-utilizing bacteria are particularly beneficial for food compositions as defined herein. Again, these lactic acid-producing bacteria are viable as defined herein.

The inventive composition may be provided as liquid composition ready to be administered (i.e. a "baby formula", "baby milk") or as dried composition (i.e. a "baby milk powder", "supplement") to be reconstituted with water prior use. For preservation of viability during storage and until consumption of the probiotic-containing product the probiotic can only be supplied in a dried form with the formula (either liquid or powdered).

In the case of a liquid composition, the viable bacteria are supplied separate from the product in a dried form (a "supplement") which can be added before use. In this embodiment, the invention provides a kit of parts, the first part being a solid dosage form comprising the living bacteria and the second part being a liquid product (such as a baby milk) free of living bacteria.

In the case of a dry composition (such as a milk powder), it is preferred that the composition of the dried infant formula containing the viable bacteria has a water activity below 0.2, preferably below 0.15 to further increase shelf stability. Low water activity reduces the rate of degradation of powders and blocks the growth and activity of microbes. Water activity values below 0.2 which correspond to water content of ca. 5%, preferably lower in the range from 2.5 to 3.5%, or lower are typically used to block lactose crystallization, and considerably decrease the rate of chemical and enzymatic reactions in milk powders.

In a second aspect, the invention relates to the use of the inventive composition as pharmaceuticals, particularly for treatment of digestive diseases. The compositions described herein provide a useful bacterial consortium able to promote or re-establish a healthy gut colonization in humans, particularly infants. This aspect of the invention shall be explained in further detail below.

The compositions of the invention have therapeutic and/or preventive effects, and may be used especially for the treatment of digestive diseases in infants or patients in need thereof, or for reducing the risk of digestive diseases in infants or patients in need thereof, or for reducing the severity of digestive diseases in infants or patients in need thereof.

Accordingly, the invention also provides for a composition as described herein as pharmaceutical.

The invention further provides for:
- the use of a composition as described herein for the manufacture of a medicament for the treatment of digestive diseases or disorders;
- the therapeutic use of a composition as described herein;
- a method of treatment of digestive disease or disorder comprising the step of administering an effective amount of a composition as described herein to a subject in need thereof;
- a composition as described herein for the treatment of digestive diseases or disorders; and/or
- a composition as described herein for use in the treatment of digestive diseases or disorders.

The inventive compositions comprise viable bacteria as defined herein in an amount sufficient to at least partially promote a health benefit. An amount to accomplish this is defined as a "therapeutically effective dose". Amounts effective for this purpose will depend on a number of factors known to those of skill in the art such as the weight and general health status of the human to be treated, and on the effect of the food matrix. In prophylactic applications, the inventive compositions are administered to a consumer susceptible to or otherwise at risk of a disorder in an amount that is sufficient to at least partially reduce the risk of developing a disorder as defined herein. Such an amount is defined as a "prophylactic effective dose". Amounts effective for this purpose will depend on a number of factors known to those of skill in the art such as the weight and general health status of the human to be treated, and on the effect of the food matrix.

Without being bound to theory, it is believed that the scientific rational behind the present invention may be summarized as follows:

(1) The infant gut microbiota contains a large and highly diverse population of lactate producing bacteria (mainly *Bifidobacteria, Lactobacilli, Streptococci* and *Staphylococci*). Many other species shaping the lactate utilizing community (LUB) also colonize the intestine of infants at early stage, comprising sulfate reducing bacteria (SRB) and non SRB (=LUB). In infants, the LUB population is mainly dominated by *E. hallii* and *Veillonella*. Therefore, an intense competition for lactate occurs in the GIT tract involving *E. hallii, Veillonella* and SRB. SRB and *E. halli* dominate the infant intestine microbiota during the first 3 months of life, together with *Veillonella*, which population will further increase at 4 months.

(2) High LUB populations are found and stratified by screaming. LUB are promoted in these infants and there is likely a huge competition for lactate. Screaming could be a consequence of this bacterial competition in the GIT by promoting the growth of certain microbes or production of deleterious bacterial metabolites.

(3) Lactate utilizing propionate producing bacteria could therefore dominate the community at an early stage impacting the global equilibrium of this bacterial community. The objective would be to decrease SRB and *E. hallii* populations or metabolites produced. Indeed, SRB produces $H_2S$ while *E. hallii* produces a lot of H2 which are both associated to pain and intestinal discomfort in humans.

(4) Lactate utilizing propionate producing bacteria can convert intestinal lactate into propionate and then remove it from the gut ecosystem. This approach prevents any lactate accumulation but also impacts growth and metabolism of other lactate utilizing bacteria which produce negative compounds potentially involved in infant screaming and colics.

The present inventors now realized that lactate utilizing propionate producing bacteria could reduce $H_2S$ and H2 production in colicky babies by creating a healthier and balance trophic chain in the first month of life. In a preferred embodiment, the digestive disorder therefore is infantile colic (also termed "IC" or "infant colic" or "baby colic").

In a further preferred embodiment, the digestive disease or disorder is selected from the group consisting of colics, intestinal discomfort, intestinal pain, visceral sensitivity and intestinal cramp.

In a further preferred embodiment, the digestive disease is colitis.

In a further embodiment, the inventive compositions are used to prevent lactate accumulation in a patient's (particularly infant's) gut. It is believed that such malfunction may otherwise lead to acidosis and/or colics.

In a further embodiment, the inventive compositions are used to decrease H2S production in a patient's (particularly infant's) gut. It is believed that such use prevents colics and/or colitis.

In a further embodiment, the inventive compositions are used to mimic the trophic chain observed in breast milk. It is believed that this provides optimum nutrition for newborns.

In a further embodiment, the inventive compositions are used to control, or to normalize intestinal colonization and gut ecology. It is believed that this improves gut health.

As outlined above, a particularly relevant group of patients are newborn babies. It was found that babies born by caesarean are a particularly important group of patients to be treated. However, the invention is not limited to this specific group of patients, but may be useful for the treatment of (i) newborn babies (typically less than 1 month), (ii) infants (typically less than 12 months) and (iii) young children (typically less than 36 months).

In a third aspect, the invention relates to a process for manufacturing a composition as described herein. This aspect of the invention shall be explained in further detail below:

The starting materials, including viable (living) bacteria strains, are known or obtainable according to known methods. The manufacturing of the inventive compositions depends largely on the final product type: dry product, i.e., a solid form (such as a powder) or wet product, i.e. a liquid (such as a drink) or semi-liquid (such as a mash).

Generally, all methods known for manufacturing food products comprising viable (living) bacteria may be employed. Typically, the food product is produced, and a formulation of living bacteria is added.

Generally, the viable bacteria may be cultured according to any suitable method and prepared for addition to the inventive composition by freeze-drying or spray-drying, for example. Details may be found in Lacroix, et al (Microbial production of food ingredients, enzymes and nutraceuticals, McNeil, Giavasis, Harvey Eds. Woodhead Publishing Ltd, Cambridge, (2012)), which is incorporated by reference. Alternatively, bacterial preparations can be obtained from specialist already prepared in a suitable form for addition to the inventive compositions.

In a preferred embodiment, the inventive composition is a milk powder. Milk powder production is a well-established technology and described e.g. in Walstra (Dairy science and technology. 2nd ed., Boca Raton: Taylor & Francis, 782 pp. (2006)) and Schuck (Milk Powder: Types and Manufacture. In Encyclopedia of Dairy Sciences (Second Edition), Academic Press, Pages 108-116 (2011)), both incorporated by reference.

For example, an inventive composition may be prepared by blending together protein source, carbohydrate source, and fat source in appropriate proportions. If used, the emulsifiers may be included in the blend. Vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture.

The liquid mixture may then be thermally treated to reduce bacterial loads. For example, the liquid mixture may be rapidly heated to a temperature in the range of about 80° C. to about 110° C. for about 5 seconds to about 5 minutes. This may be carried out by steam injection or by heat exchanger; for example, a plate heat exchanger.

The liquid mixture may then be cooled to about 60° C. to about 85° C.; for example, by flash cooling. The liquid mixture may then be homogenized; for example, in two stages at about 7 MPa to about 40 MPa in the first stage and about 2 MPa to about 14 MPa in the second stage. The homogenized mixture may then be further cooled to add any heat sensitive components; such as vitamins and minerals. The pH and solids content of the homogenized mixture is conveniently standardized at this point. The homogenized mixture is transferred to a suitable drying apparatus such as a spray drier or freeze drier and converted to powder. The powder should have a moisture content of less than about 5% by weight.

To further illustrate the invention, the following examples are provided. These examples are provided with no intent to limit the scope of the invention.

TABLE 1

| Protein (g/100 kcal) | 2.5 | 2.5 | 2 | 2.5 | 2 |
|---|---|---|---|---|---|
| Whey/Casein | 40/60 | 40/60 | 50/50 | 40/60 | 50/50 |
| CHO (g/100 kcal) | 12.9 | 12.9 | 12.3 | 12.9 | 12.3 |
| Lactose (g/100 kcal) | 9 | 12.9 | 7.7 | 12.9 | 7.7 |
| Maltodextrine (g/100 kcal) | 3.9 | | 4.6 | | 4.6 |
| Fat (g/100 kcal) | 4.25 | 4.25 | 4.8 | 4.25 | 4.8 |
| viable bacteria (per g formula dry weight) | (1) $2 \times 10^8$ | (2) Each: $1 \times 10^8$ | (3) Each: $1 \times 10^8$ | (4) $2 \times 10^8$ | (5) $2 \times 10^8$ |
| Prebiotic LC-PUFA | (6) | (6) | (6) | (6) DHA | (6) ARA/DHA |
| Energy (Kcal/100 mL) | 64.88 | 64.88 | 65 | 64.88 | 65 |

Table 1: An age-tailored set of nutritional compositions for infant or young children according to the present invention. Specifications of the bacteria included are as follows:
(1) *P. freudenreichii*;
(2) *P. freudenreichii* and *Bifidobacterium lactis* BB12;
(3) *P. freudenreichii* and *Lactobacillus rhamonosus* GG;
(4) *Megasphera elsdensii*
(5) *Veillonella parvula*;
(6) Optionally GOS.

EXAMPLE 1

In this example, the effect of supplementation of *C. avidum* (*Cutibacterium avidum*) on colonization potential and metabolic effects in artificial infant microbiota is measured.

Bacterial strains and growth conditions: Reference strains used in this study were obtained from the German Collection of Microorganisms and Cell Cultures (DSMZ, Braunschweig, Germany) and from the strain collection of the Laboratory of Food Biotechnology. *Propionibacterium/Cutibacterium* were routinely grown in yeast extract sodium lactate medium (YEL) consisting of 1% (w/v) trypticase soy broth without dextrose (Becton Dickinson AG, Allschwil, Switzerland), 1% (w/v) yeast extract (Merck, Darmstadt, Germany), 117 mM sodium DL-lactate (60% v/v syrup, Central Drug House, New Delhi, India), 0.025% (w/v) KH2PO4 (VWR International AG, Dietikon, Switzerland) and 0.0005% (w/v) MnSO4 (Sigma-Aldrich, Buchs, Switzerland). Glycerol stocks stored at −80° C. were reactivated on agar plates and were grown in airtight jars (Mitsubishi AnaeroPack, Thermo Fisher Diagnostics AG, Pratteln, Switzerland) containing one AnaeroGen sachet (Oxoid, Thermo Fisher Diagnostics AG) at 37° C. for 5 days. Single colonies were then inoculated into liquid YEL and incubated for 48 h at 37° C. before further use.

To enhance selectivity of YEL for the isolation of *Propionibacterium/Cutibacterium* from infant feces, kanamycin (0.01% m/v Sigma-Aldrich) and/or metronidazole (0.004% m/v Sigma-Aldrich) were added. Kanamycin inhibits the growth of Gram-negative bacteria while metronidazole reduces growth of anaerobic microorganisms like *Bacteroides* and *Peptostreptococcus*. *Propionibacterium/Cutibacterium* are intrinsically resistant to metronidazole (Tally et al. 1978). To confirm that antibiotic addition did not affect the growth of *Propionibacterium/Cutibacterium*, ten-fold dilution series of selected isolates grown in YEL broth for 48 h were spread-plated onto YEL, and YEL supplemented with kanamycin (YEL-K), metronidazole (YEL-M), or a combination (YEL-K-M). In order to test the capacity of detection of *Propionibacterium/Cutibacterium* colonies in complex microbiota samples, one mL of a 10% (w/v) dilution in peptone water (Oxoid AG, Pratteln, Switzerland) of a fresh fecal sample, was spread-plated onto YEL, YEL-K, YEL-M and YEL-K-M. Aliquots of the same fecal sample were spiked with 10 μL of 48 h liquid culture of selected strains and results of enumeration were compared. Cell counts were expressed in colony forming units (CFU) $mL^{-1}$ using the arithmetic weighted mean.

*C. avidum* strains used for supplementation of in vitro colonic fermentation were sub-cultured every 24 h (1% v/v) in YEL broth and incubated at 37° C. Reactor inoculum cultures were centrifuged for 10 min at 8000 g, the supernatant was removed, and the pellet was re-suspended in sterile peptone water (Oxoid AG). The final dose added to treatment reactors (TRs) was approximately $10^{10}$ CFU *C. avidum* (TR 1, 2 and 3) or $2*10^{11}$ CFU (TR4).

Experimental set up: A PolyFermS continuous intestinal fermentation model inoculated with immobilized infant fecal microbiota was operated with proximal colon section conditions. The fermentation set-up consisted of a two-stage reactor design, as depicted in FIG. 1. The fermentation model was inoculated with immobilized fecal microbiota from a 2 months old infant and consisted of a first-stage inoculation reactor (IR) containing fecal beads and five second-stage reactors, one control reactor (CR) and four treatment reactors (TR1, TR2, TR3 and TR4) continuously inoculated with 5% IR effluent. All reactors operated under the same conditions, modelling the infant proximal colon. The first-stage inoculation reactor (IR) contained 30% (v/v) immobilized fecal microbiota (1-2 mm diameter gel beads) prepared with a fecal sample obtained a healthy male, aged 39 days, born by vaginal delivery, exclusively formula-fed with no antibiotic administered. Fermentation stability was monitored daily by HPLC-RI analysis of concentration of SCFA and intermediate metabolites in the effluent of reactors.

The second-stage reactors were tested in three consecutive periods as displayed in Table 2, reproduced below:

stabilization of all reactors (Period A, 10 days). Period B (7 days) included a daily spiking of TR 1-3 with one of three non-hemolytic C. avidum (P278, P279 and P280) isolates at a concentration of $10^8$ CFU mL$^{-1}$ reactor effluent, while TR4 was spiked with strain P279 at $10^9$ CFU mL$^{-1}$. In period C (7 days), C. avidum was spiked as in period B but with addition of 30 mM potassium-L-lactate (60% v/v solution, Sigma Aldrich). During periods B and C, C. avidum was added daily to TR in a final suspension volume of 4 mL; an equal volume of sterile peptone water (Oxoid AG) was added to the CR to avoid possible bias due to dilution. Addition of 30 mM potassium-L-lactate (60% v/v solution, Sigma Aldrich) continued during period D (7 days) as in period C, but without C. avidum spiking to test for washout or persistence of the added strains.

(triangle) and TR4 (triangle) at day 5, 6 and 7 of wash-out (period D). The dashed line indicates the minimum detection level for the enumeration (plated dilutions: $10^{-3}$ to $10^{-6}$).

This effect of spiking is supported by qPCR data that indicated increased abundance of Propionibacterium/Cutibacterium in TR1 (log 6.1±0.2 cells mL$^{-1}$) and TR4 (log 7.2±0.04 cells mL$^{-1}$) compared to CR (below detection limit) and by 16S rRNA gene libraries. During period C, supplying L-lactate further increased C. avidum numbers in TR4 (spiked at $10^9$ CFU mL$^{-1}$; log 9.2±0.08 CFU mL$^{-1}$) compared to the previous period C (log 8.9±0.1 CFU mL$^{-1}$). The abundance of C. avidum measured by plate count during the washout period in the presence of L-lactate (period D) decreased over time, reaching levels comparable to CR in TR2 after 120 h, and in TR1 and TR3 after 170 h. In contrast,

TABLE 2

| Period | | Days | TR1 | TR2 | TR3 | TR4 | CR |
|---|---|---|---|---|---|---|---|
| A | Stabilization | 10 | No intervention | No intervention | No intervention | No intervention | No intervention |
| B | Spiking | 7 | C. avidum P278 $10^8$ CFU mL$^{-1}$ | C. avidum P279 $10^8$ CFU mL$^{-1}$ | C. avidum P280 $10^8$ CFU mL$^{-1}$ | C. avidum P279 $10^9$ CFU mL$^{-1}$ | No intervention |
| C | Spiking + Lactate | 7 | C. avidum P278 $10^8$ CFU mL$^{-1}$ + 30 mM potassium-L-lactate | C. avidum P279 $10^8$ CFU mL$^{-1}$ + 30 mM potassium-L-lactate | C. avidum P280 $10^8$ CFU mL$^{-1}$ + 30 mM potassium-L-lactate | C. avidum P279 $10^9$ CFU mL$^{-1}$ + 30 mM potassium-L-lactate | 30 mM potassium-L-lactate |
| D | Wash out + Lactate | 7 | 30 mM potassium-L-lactate | 30 mM potassium-L-lactate | 30 mM potassium-L-lactate | 30 mM potassium-L-lactate | 30 mM potassium-L-lactate |

Table 2. Experimental conditions at different fermentation periods. The stabilization period (A) lasted 10 days until all reactors reached equal conditions. Each intervention period lasted 7 days each and were defined as spiking (B); spiking + lactate (C); and wash-out with lactate (D). During spiking (period B), C. avidum infant isolates were added to each TRs to reach a concentration of $10^8$ cells mL$^{-1}$ (TR1 was spiked with strain P278, TR2 with P279 and TR3 with P280). TR4 spiked with P279 at $10^9$ cells mL$^{-1}$. During spiking + lactate (period C), 30 mM potassium-L-lactate was added to feeding medium for TRs and CR, while spiking continued as in period B. During wash out (period D) addition of 30 mM potassium-L-lactate proceeded for 7 days, whereas the spiking with C. avidum isolates was cancelled.

Samples from the reactor effluents of the last three days of each period were used to analyze bacterial composition (16S rRNA gene amplicon sequencing and qPCR), enumeration of C. avidum in YEL-K-M agar and metabolite analysis by HPLC-RI (described below). A theoretical washout curve was calculated with the formula $Ct=C0*EXP(4/RT)$ where RT is the mean retention time (5 h) and C0 and Ct are cell concentrations at time 0 and t, respectively, and compared with C. avidum numbers measured in TRs. Assessment of bacterial composition by qPCR and 16S rRNA gene amplicon sequencing was performed for effluents of CR and TR1 and TR4. Viable cell numbers and fermentation metabolite profiles were determined for all reactor effluents.

Figure 2A:
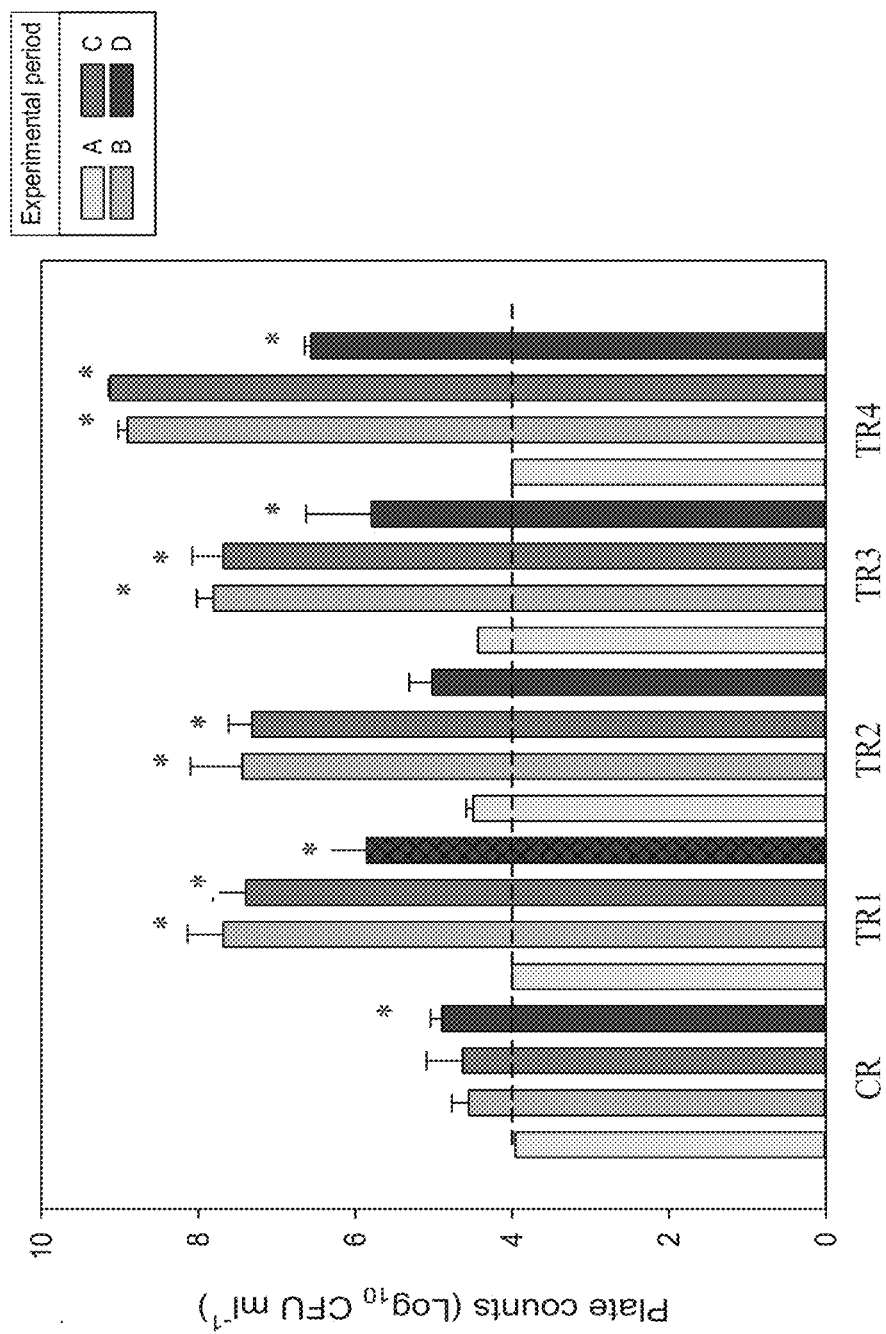
FIG. 2A is a bar graph showing C. avidum concentration in a control reactor (CR) and four treatment reactors (TRs) during the intervention periods, according to Example 1 described herein.

Impact of treatments on C. avidum abundance: During spiking of isolates (period B), mean abundance of viable C. avidum measured by plate counting in TRs 1-3 (log 7.6±0.2 CFU mL$^{-1}$) and TR4 (log 8.9±0.1 CFU mL$^{-1}$) were significantly higher (p<0.05) compared to CR (log 4.6±0.2 CFU mL-1), as depicted in FIG. 2A. FIG. 2A depicts a bar graph showing C. avidum concentration ($\log_{10}$ CFU mL$^{-1}$) in CR and TRs during the intervention periods estimated by culture. Reported values are means and standard deviations for combined samples from the last 3 days of each experimental period. Values marked by an asterisk are significantly different from the value for the same reactor during stabilization period (p<0.05).

Figure 2B:
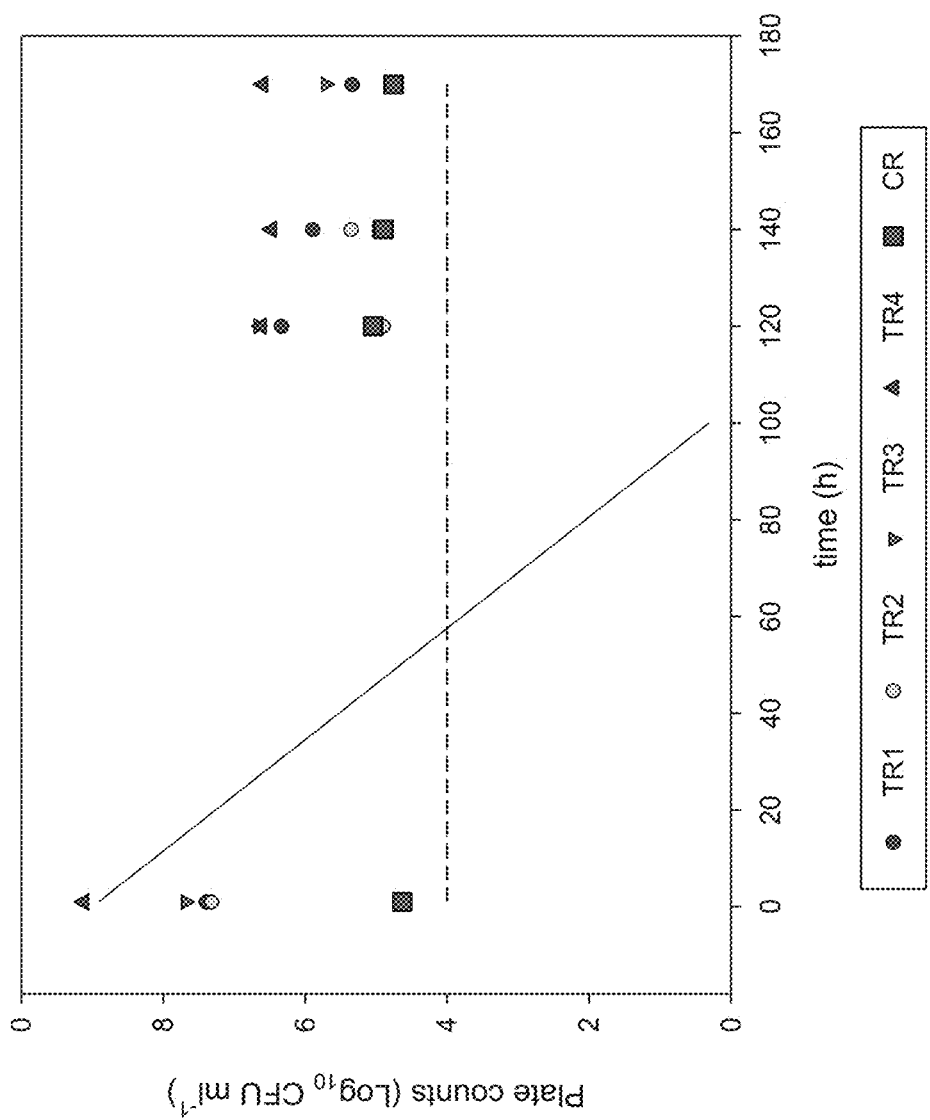
FIG. 2B is a graph showing C. avidum concentration in reactor effluents compared to a theoretical washout curve, according to Example 1 described herein.

FIG. 2B depicts C. avidum concentration (log 10 CFU mL$^{-1}$) in reactor effluents compared to a theoretical washout curve calculated for a perfectly mixed stirred-tank reactor with a mean retention time of 5 h. The solid line indicates the theoretical wash-out curve at initial spiking concentrations of $10^9$ CFU mL$^{-1}$. Symbols indicate C. avidum concentration in CR (full square) and TR1 (circle), TR2 (circle), TR3 high and steady C. avidum abundance was measured in TR4 between 120 and 170 h, suggesting stable colonization of the isolate.

Impact of C. avidum and L-lactate supplementation on microbiota composition: Shifts in microbiota composition induced by treatments were evaluated by comparing to the previous period within the same reactor. The addition of C. avidum during period B led to an increase in the proportion of total propionate-producing bacteria (from 14% to 18% in TR1 and 17% to 25% in TR4). Within the group of propionate-producing bacteria, the relative abundance of Propionibacterium/Cutibacterium increased from 0% to 1% in TR1 while Veillonella decreased (13% to 11%, log 8.4±0.3 to 7.8±0.3 gene copies). In TR4 spiked with tenfold higher levels of C. avidum, relative abundance of Propionibacterium/Cutibacterium increased from 0% to 20%, with a consequent reduction of Bacteroides (45% to 36%, log 9.6 to log 9.0 gene copies), Prevotella (35% to 24%) and Veillonella (12% to 11%, log 8.3±0.1 to 7.5±0.1 gene copies), as depicted in FIG. 3A. FIG. 3A depicts the effect of C. avidum and L-lactate supplementation on potential propionate-producers of the PolyFermS microbiota in the form of a heat-map showing the relative abundance at genus level of potential propionate producers identified by 16S rRNA gene amplicon sequencing in fermentation effluent for CR, TR1 and TR4.

Figure 3B:
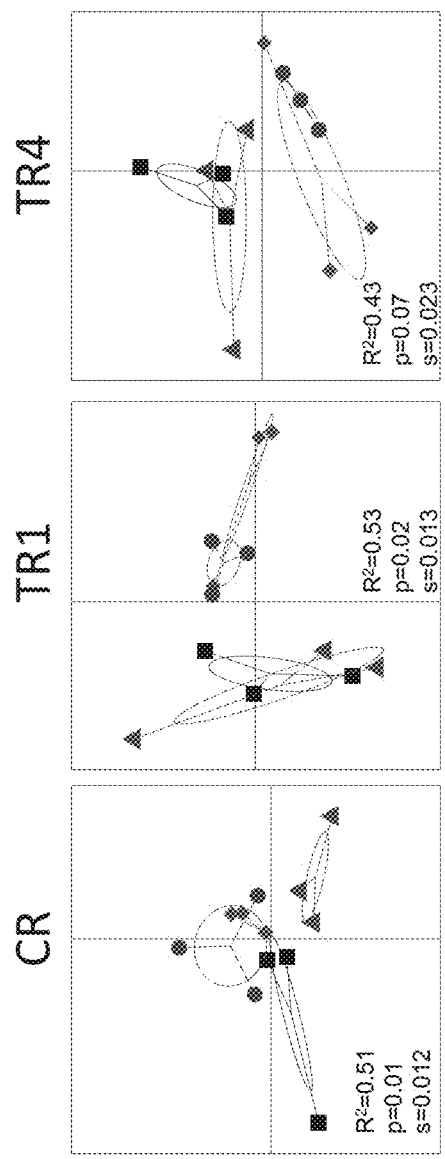
FIG. 3B is a principal coordinate analysis plot based on weighted UniFrac distances based on 16S rRNA gene amplicon sequencing, according to Example 1 described herein.

In general, adding lactate with C. avidum (period C) had a greater impact on microbiota composition than C. avidum supplementation alone, as depicted in FIGS. 3A & 3B. FIG. 3B depicts the effect of C. avidum and L-lactate supplementation on beta diversity of the modelled microbiota in the form of a principal coordinate analysis plot based on weighted UniFrac distances based on 16S rRNA gene amplicon sequencing in fermentation effluent from the last 3 days of each period for CR, TR1 and TR4. The circles represent samples from stabilization (period A), the diamonds represent spiking (period B), the squares represent spiking +30 mM potassium-L-lactate (period C) and the triangles represent wash out with lactate (period D).

Log 16S rRNA gene copies of the bacterial groups analyzed by qPCR were not affected in CR, TR1 and TR4, but relative abundance (16S RNA sequencing) of *Eubacterium* (2322 fold for CR, 877 fold for TR1 and 2 fold for TR4), *Veillonella* (2.8-3.6 fold) and *Lactobacillus* (2.1-3.8 fold) increased with lactate addition, while *Bacteroides* decreased (0.3-0.7 fold). An increase in the total abundance of propionate-producing bacteria (from 21% to 31%), associated with an increase of *Veillonella* (from 19% to 46%), was observed in CR during period C compared to period B without lactate (FIG. 3A). During period D, relative abundance of *Propionibacterium* decreased below the detection level in TR1 and TR4, while, among the potential propionate-producing taxa, the abundance of *Prevotella* increased (37% to 41% in TR1 and from 25% to 42% in TR4).

The association between 16S rRNA gene relative abundance of *Propionibacterium/Cutibacterium* and other taxa in TR1 and TR4 was tested using Spearman's correlation analysis. *Propionibacterium/Cutibacterium* was negatively correlated (p<0.05) to *Collinsella* and *Enterococcus* and positively correlated (p<0.05) to *Lactobacillus, Finegoldia, Peptoniphilus, Parabacteroides* and *Dialister*.

Impact of *C. avidum* and L-lactate supplementation on metabolite formation: The metabolic impact of *C. avidum* addition was evaluated by comparison to the previous period within the same reactor. Addition of *C. avidum* at $10^8$ CFU mL$^{-1}$ (TR 1-3) slightly reduced formate production (significant for TR3). Addition of *C. avidum* at $10^9$ CFU mL$^{-1}$ (TR4) increased propionate (14 to 21 mM), butyrate (4.5 to 6.4 mM) and total SCFA (98.6 to 111.4 mM). The L-lactate that was supplemented to all reactors during period C was almost completely utilized (detected at below 1 mM), while total SCFA (12.9-32.8 mM), acetate (5.1-13.2 mM), propionate (2.9-11.4 mM) and butyrate (3.6-7.4 mM) increased compared to period B in each reactor. Formate increased significantly (from 24 to 30 mM) in CR with lactate addition but not in TRs being spiked with *C. avidum*. There were no major shifts in metabolic activity of TRs after omission of *C. avidum* addition (period D). *C. avidum* spiked daily at $10^8$ or $10^9$ cells mL$^{-1}$ colonized, decreased formate, and persisted during the washout period. Significant correlations were observed between *Propionibacterium/Cutibacterium* and lactate-producers and protein-degraders in both reactors and infant feces.

The findings highlight the natural presence of *C. avidum*, and its role as a lactate consumer and propionate-producer in infants younger than 3 months. The ability of *C. avidum* to stably colonize in modelled infant microbiota in conditions mimicking the proximal colon section of a colicky infant (high lactate production), and to induce consistent metabolic shift towards acetate and propionate production while inhibiting lactate-utilizing bacteria producing high amount of hydrogen gas, such as *Veillonella*, was also shown.

EXAMPLE 2

In this example the effect of supplementation of *C. avidum* (*Cutibacterium avidum*) on gas production in gnotobiotic rats colonized with colonic infant fecal microbiota is measured.

Figure 4:
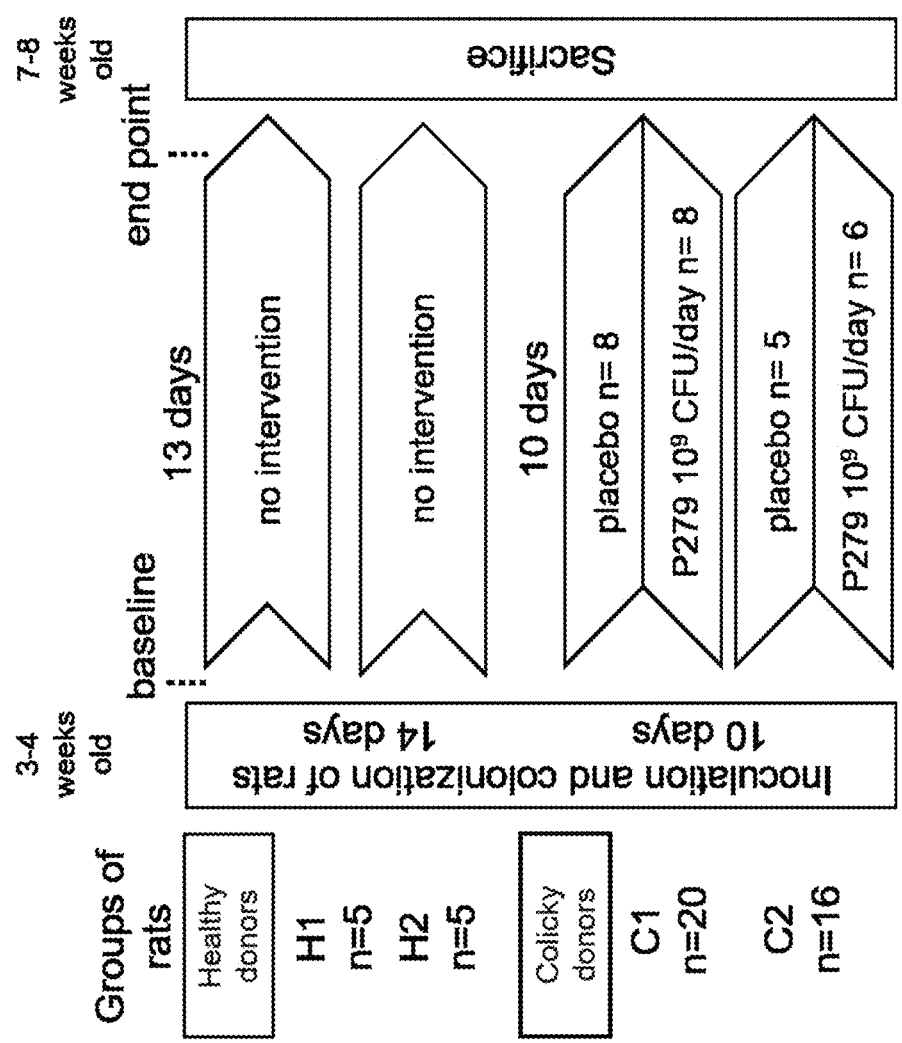
FIG. 4 is a schematic diagram of the study design conducted in Example 2 described herein.

Donors and sample collection: FIG. 4 depicts a study design for an infant microbiota-associated (IMA) rat study, colonized with healthy (H1 and H2) and colicky (C1 and C2) fecal microbiota. Fecal samples from two healthy infants (H1: 59 days old and H2: 92 days old) and two infants suffering from IC (C1: 71 days old and C2: 68 days old) who satisfied the Rome III criteria were used for inoculation of germ-free Fischer 344 rats. Inclusion criteria were: a full-term delivery (gestation time 37-42 weeks), normal birth weight (female: 2.7-5.0 kg; male: 2.9-5.2 kg) and exclusively milk-based diet. Exclusion criteria were: sickness and history of antibiotic treatment. Healthy infants did not present gastroenterological disorders while colicky donors complied with the 3 diagnostic criteria for IC: i, paroxysms of irritability, fussing, or crying that start and stop without obvious cause; ii, episodes lasting 3 or more hours per day and occurring at least 3 days per week for at least 1 week; iii, no failure to thrive. Parents of donors were asked to provide a single fecal sample to a study nurse, and data and material were subsequently anonymized. Anonymized biological material is not under the scope of the Swiss Federal Human Research Act (Art. 2 para. 2 let. b and c), which excluded this study from requiring ethical approval. Fecal samples were collected from diapers into 50 mL sterile conical shaped polypropylene tubes and placed into closed airtight jars (Thermo Fisher Diagnostics AG) containing one AnaeroGen sachet (Oxoid). Samples were kept cool with frozen gel packs and transported into a Styrofoam box until further processing (within 48 h of sampling).

Experimental set-up: Germ-free Fischer 344 rats were kept in sterile isolators with positive pressure over the entire trial period. Rats were weaned at 3-4 weeks of age and were inoculated with infant fecal microbiota slurries (1000-fold dilution of fecal sample in anaerobic mineral solution) from a single donor by a single intra-gastric gavage. After inoculation, the microbiota was allowed to establish before further measurements. For analysis, feces from IMA rats were collected directly from the anus by manual perineal stimulation and immediately used for microbial enumeration or stored at −80° C. until further processing. The amount of H2 excreted by each IMA rat was measured by housing single animals in a respiratory chamber for 24 h. Hydrogen excretion measurements were done at day 27. Baseline measurements from IMA rats inoculated with fecal microbiota from colicky donors C1 and C2 were obtained at day 10 after inoculation. In the following 10 days, treatment groups were gavaged daily with $10^9$ colony forming units (CFU) of *C. avidum* P279 and control groups were given 350 μL of sterile skim milk. Feces collection, fecal microbial enumeration and H2 excretion measurements were obtained again at day 7-10 of intervention. Rats were sacrificed at 8 weeks of age and the caecum contents were harvested for measurements of fermentative end-products.

Housing and diet: Twenty female germ-free rats were inoculated with fecal slurries from donor C1, and two groups of 6 rats each were allocated in two different isolators. Rats were fed with a gamma irradiated infant formula (Aptamil Pre, Milupa GmbH, Germany) and added one pellet per day of standard diet for growing rats (A03/R03, SAFE, France) to mimic an infant diet and keep healthy rats. Fecal microbiota from donor C2 was inoculated in 16 germ-free rats and separated in two groups placed in different isolators. The treatment group had 4 female and 2 male rats and the control group, 2 females and 3 males. All rats were given free access to sterilized water. All experimental protocols were approved by the Local Institutional Animal Care and Use Committee.

Bacterial strains and growth conditions: *C. avidum* P279 was obtained from the strain collection of the Laboratory of Food Biotechnology (ETH, Zurich, Switzerland) and was grown in yeast extract sodium lactate medium (YEL) consisting of 1% (w/v) trypticase soy broth without dextrose (Becton Dickinson AG, Allschwil, Switzerland), 1% (w/v) yeast extract (Merck, Darmstadt, Germany), 117 mM sodium DL-lactate (60% v/v syrup, Central Drug House, New Delhi, India), 0.025% (w/v) KH2PO4 (VWR International AG, Dietikon, Switzerland) and 0.0005% (w/v) MnSO4 (Sigma-Aldrich, Buchs, Switzerland). Glycerol stocks stored at −80° C. were reactivated on agar plates and were in airtight jars (Mitsubishi AnaeroPack, Thermo Fisher Diagnostics AG, Pratteln, Switzerland) containing one AnaeroGen sachet (Oxoid, Thermo Fisher Diagnostics AG) at 37° C. for 5 days. Single colonies were then inoculated into liquid YEL and incubated for 48 h at 37° C. After incubation, cultures were centrifuged for 10 min at 7000 g and pellets were re-suspended in the same volume of sterile reconstituted skim milk (10% w/v). Aliquots of 350 µL (approximately $10^9$ CFU of *C. avidum* P279) were transferred into cryovials (Huber Co, Reinach, Switzerland). For supplementation of the control group, aliquots of 350 µL of sterile reconstituted skim milk (10% w/v) were also prepared in cryovials (Huber Co). Cryovials were snap-frozen in liquid nitrogen and stored at −80° C. until supplementation.

Microbial analyses: Fresh feces from donors and IMA rats were 10-fold diluted (wet w/v) in an anaerobic mineral solution. Total anaerobes, SRB-producing and non-SRB LUB communities were enumerated by the Most Probable Number estimation (MPN) with three liquid culture tubes inoculated per dilution for each selective medium in $O_2$-free $CO_2$ sparged Hungate tubes sealed with butyl-rubber stoppers (Dutscher SAS, Brumath, France). Total anaerobes were enumerated in a clarified rumen fluid containing medium. Lactate-utilizing not reducing sulfate (LUB-non SRB) were enumerated in L-lactate (35 mM) containing basal medium. After incubation at 37° C. for 5 days, lactate concentration in media supernatant (2 mL) was determined by HPLC. Tubes with a final lactate concentration below 25 mM (lactate consumption of at least 10 mM) were considered positive. Lactate-utilizing sulfate reducing bacteria (LUB-SRB) were enumerated in the Postgate E medium and formation of black precipitate of FeS was recorded for MPN determination. *Cutibacterium* were enumerated in YEL supplemented with kanamycin [0.001% (m/v) Sigma-Aldrich] and metronidazole [0.0004% (m/v) Sigma-Aldrich] after 5 days of incubation at 37° C. *Enterobacteriaceae* were enumerated in Violet Red-Bile Dextrose Agar (Sigma-Aldrich). H2S-producing enterobacteria were enumerated counting black centered colonies in Hektoen Enteric Agar. Colonies developed on these solid media were counted after aerobic incubation at 37° C. for 24 h.

For IMA rats transfaunated with samples from donor C1, enumeration was carried out in five animals from each isolator at baseline and in six animals from treatment group and four animals from the control group after supplementation. Enumeration of non-SRB LUB was done in two animals from each group at baseline and in five animals from treatment group and three from control group after intervention. For IMA rats transfaunated with samples from donor C2, enumeration was carried out in four animals from the treatment group and in five animals from the control group at both time-points.

DNA isolation and quantitative PCR analysis (qPCR): Genomic DNA was extracted from infant or IMA rats stool samples (200 mg), using the Fast DNA SPIN kit for soil (MP Biomedicals, Illkirch, France) according to manufacturer's instructions. Reactions were performed using LightCycler 480 Real-Time PCR System (Roche Diagnostics, Rotkreuz Switzerland) and the SensiFASTSYBR No-ROX 2× mix (5 µL) and 500 nM primers (Biolab Scientifics Instruments SA, Chatel-St-Denis, Switzerland) in a total reaction volume of 10 µL. Thermal cycling started with an initial denaturation step at 95° C. for 3 min, followed by 40 cycles of a two-step PCR at 95° C. for 5 sec and at 60° C. for 60 sec. Ct values were obtained using automatic baseline and threshold settings provided by the LightCycler 480 Software, Version 1.5. Individual samples were analyzed in duplicate. To generate standards, PCR amplicons were cloned into pGEM-T Easy Vector and heterologously expressed in *E. coli* according to instructions of the supplier (Promega AG). Standard curves were prepared from ten-fold dilutions of linearized plasm ids harbouring the target gene of interest. Bacterial groups normally abundant in the infant feces were amplified using primers described previously. Melting curve analysis was conducted to confirm specificity. To calculate the cell counts for *Cutibacterium*, gene copies were corrected for multiple copies of 16S rRNA genes (n=3).

16S rRNA gene amplicon sequencing: The bacterial profiles in feces from donors and IMA rats were determined using tag-encoded 16S rRNA gene Miseq-based (Illumina, San Diego, Calif., USA) high throughput sequencing. Briefly, DNA concentration was standardized to 20 ng $µL^{-1}$. The V3 region of the 16S rRNA gene was amplified using primers including adapters for the Nextera Index Kit, NXt_388_F and NXt_518_R. One MiSeq flow cell and the V2 2×250 bp paired-end Nextera chemistry were used and were supplemented with 20% of PhiX. Library preparation and sequencing was performed at the Genomic Diversity Center of ETH Zurich. The raw datasets containing pair-ended reads with corresponding quality scores were merged and trimmed using settings as previously described. The minimum length of merged reads was 200 bp. Following analysis steps were done using Quantitative Insight Into Microbial Ecology (QIIME) open source software package (1.8.0 and 1.9.0). Purging the datasets from chimeric reads and constructing de novo Operational Taxonomic Units (OTUs) was conducted using the UPARSE pipeline and the Greengenes database as a reference. Alpha- and beta-diversity were analyzed as previously described using iterative subsampling. Taxonomic assignment of OTUs at genus level could not differentiate between *Propionibacterium* and *Cutibacterium* as the new taxonomy was not included in the reference database.

HPLC analysis with refractive index detection (HPLC-RI): Short chain fatty acids (SCFA) and lactate were determined in caecum content after centrifugation for 10 min at 13000 g. Supernatant (500 µL) was filtered through a 0.45 µM membrane (Millipore AG, Zug, Switzerland) into HPLC glass vials (Infochroma, Hitachi LaChrome, Merck, Dietikon, Switzerland) and sealed with crimp-caps. An HPLC (Hitachi LaChrome) equipped with a Security Guard Cartridges Carbo-H column (4×3 mm; Phenomenex Inc., Torrance, Calif., USA), a Rezex ROA-Organic Acid H+ column (8%, 300×7.8 mm; Phenomenex) and a refractive index detector (HPLC-RI) was used. The column was eluted with 10 mM $H_2SO_4$ (Fluka, Buchs, Switzerland) as mobile phase at a flow rate of 0.4 mL $min^{-1}$ at 25° C. SCFA and lactate were quantified using external standards.

Hydrogen sulphide in caecum supernatant: Fecal contents of each of the IMA rats were collected, centrifuged at 18 000 g for 10 min and sulfide production was determined in the supernatants by photometric kit (Sulfid-test, Merck, Germany).

Statistical analysis: Statistical significance was set at a P-value of less than 0.05 and all statistical analyses were done using SigmaPlot (Systat Software, San Jose, Calif., USA). Student's t-test for normally distributed data (Shapiro-Wilk test) was used to compare results from measurements at baseline and after treatment for rats from the same group and to compare post-mortem measurements in treatment vs. control groups. Mann-Whitney test was used when data was not normally distributed.

Figure 5B:
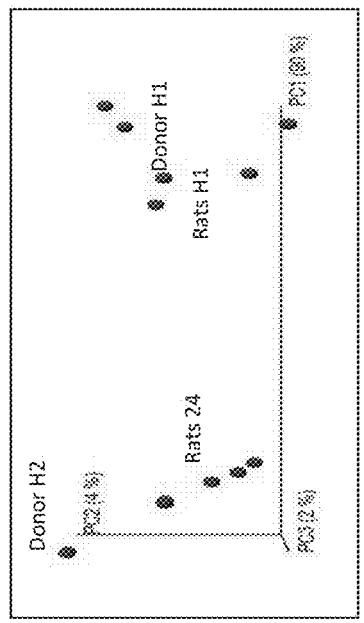
FIG. 5B is a principal coordinate analysis based on weighted UniFrac distances depicting the microbiota profile of healthy donor (H2) and corresponding IMA rat feces, according to Example 2 described herein.
Figure 5A:
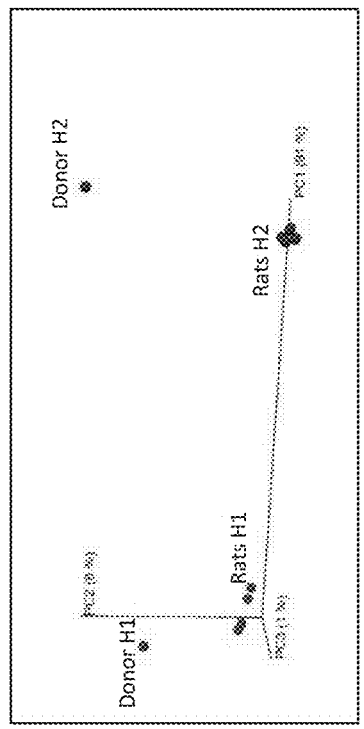
FIG. 5A is a principal coordinate analysis based on unweighted UniFrac distances depicting the microbiota profile of healthy donor (H1) and corresponding IMA rat feces, according to Example 2 described herein.
Figure 5C:
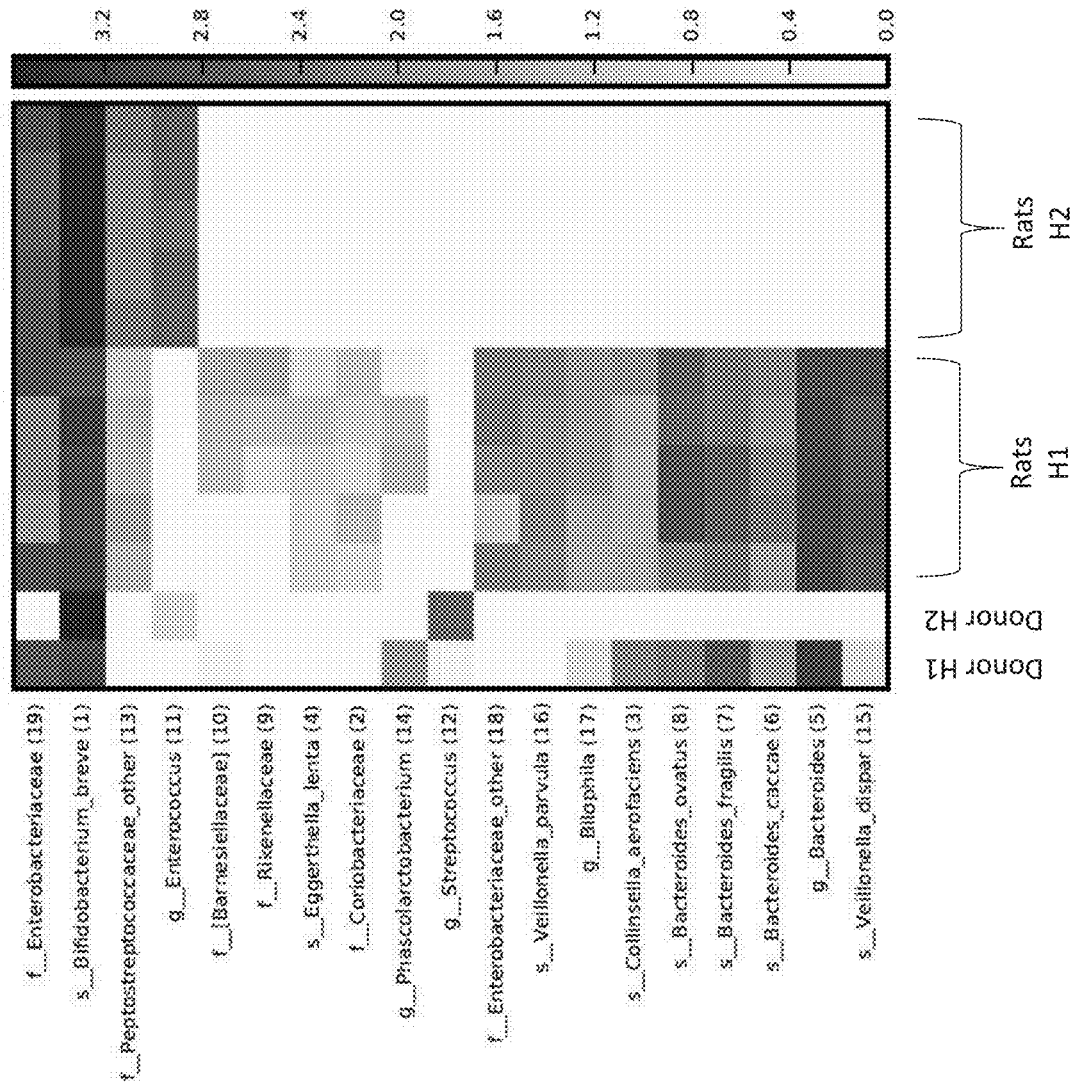
FIG. 5C is a heatmap plot of microbial groups measured by 16S RNA sequencing, according to Example 2 described herein.
Figure 6A:
FIGS. 6A and 6B are heat-maps of microbiota composition detected by 16S rRNA gene amplicon sequencing in feces from colicky infant donors (C1 and C2), according to Example 2 described herein.
Figure 6B:
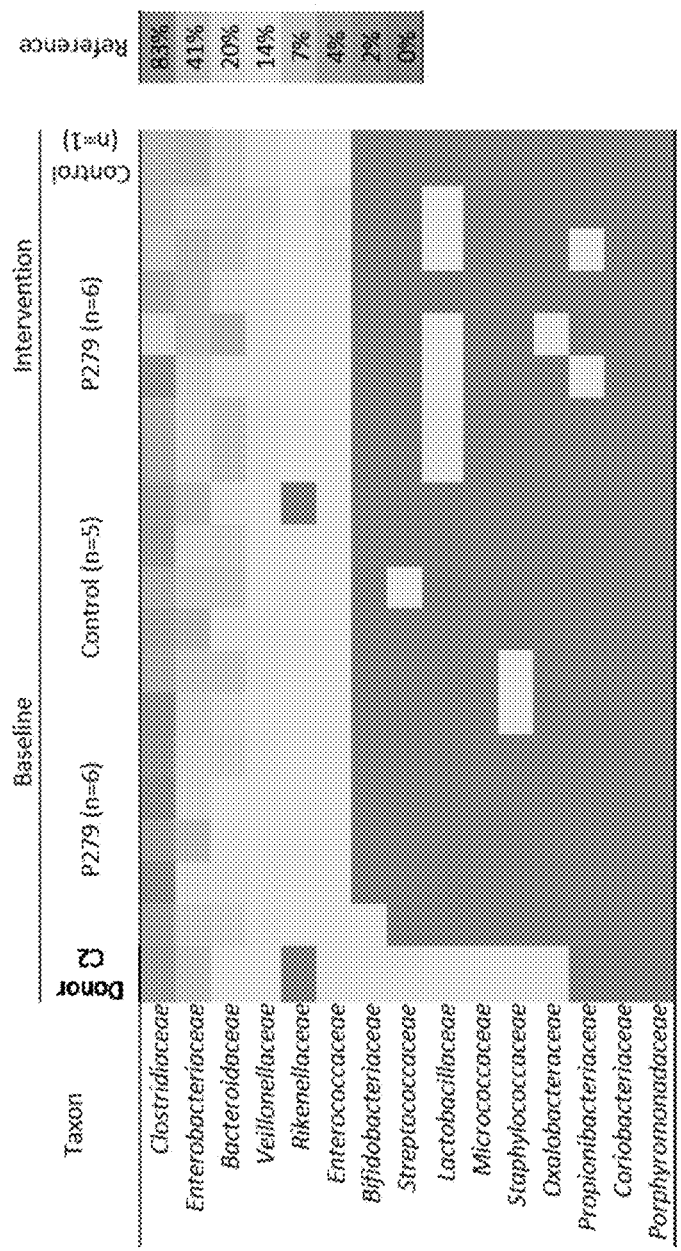

Results and discussion: FIGS. 5A-C depict the microbiota profile of healthy donor and corresponding IMA rat feces. FIG. 5A depicts the principal coordinate analysis based on unweighted UniFrac distances, with each sample represented by a circle. FIG. 5B depicts the principal coordinate analysis based on weighted UniFrac distances, with each sample represented by a circle. FIG. 5C depicts a heatmap plot of microbial groups measured by 16S RNA sequencing. FIG. 6A-B depict heat maps of microbiota composition detected by 16S rRNA gene amplicon sequencing in feces from colicky infant donors (C1 and C2) and corresponding IMA rats.

The bacterial compositions in feces of IMA rats colonized with healthy (H1 and H2) and colicky (C1 and C2) fecal microbiota and the corresponding infant feces measured by qPCR and 16S RNA sequencing were similar, except for higher colonization by *Veillonella* and lower by *Streptococacceae*, as depicted in FIGS. 5A-C and 6A-B. *Veillonella* colonized C1 and C2 rats at high numbers measured by qPCR, of Log 9.7 and Log 8.6 gene copies g feces$^{-1}$ respectively, compare to the corresponding donor feces (Log 4.6 and Log 7.5 gene copies g feces$^{-1}$, respectively) (see Table 3, reproduced below and FIGS. 6A-B). *Cutibacterium* was only detected by culture in donor feces C2, at very low level, but not in any of the rats by qPCR nor plating methods at baseline.

Figure 7:
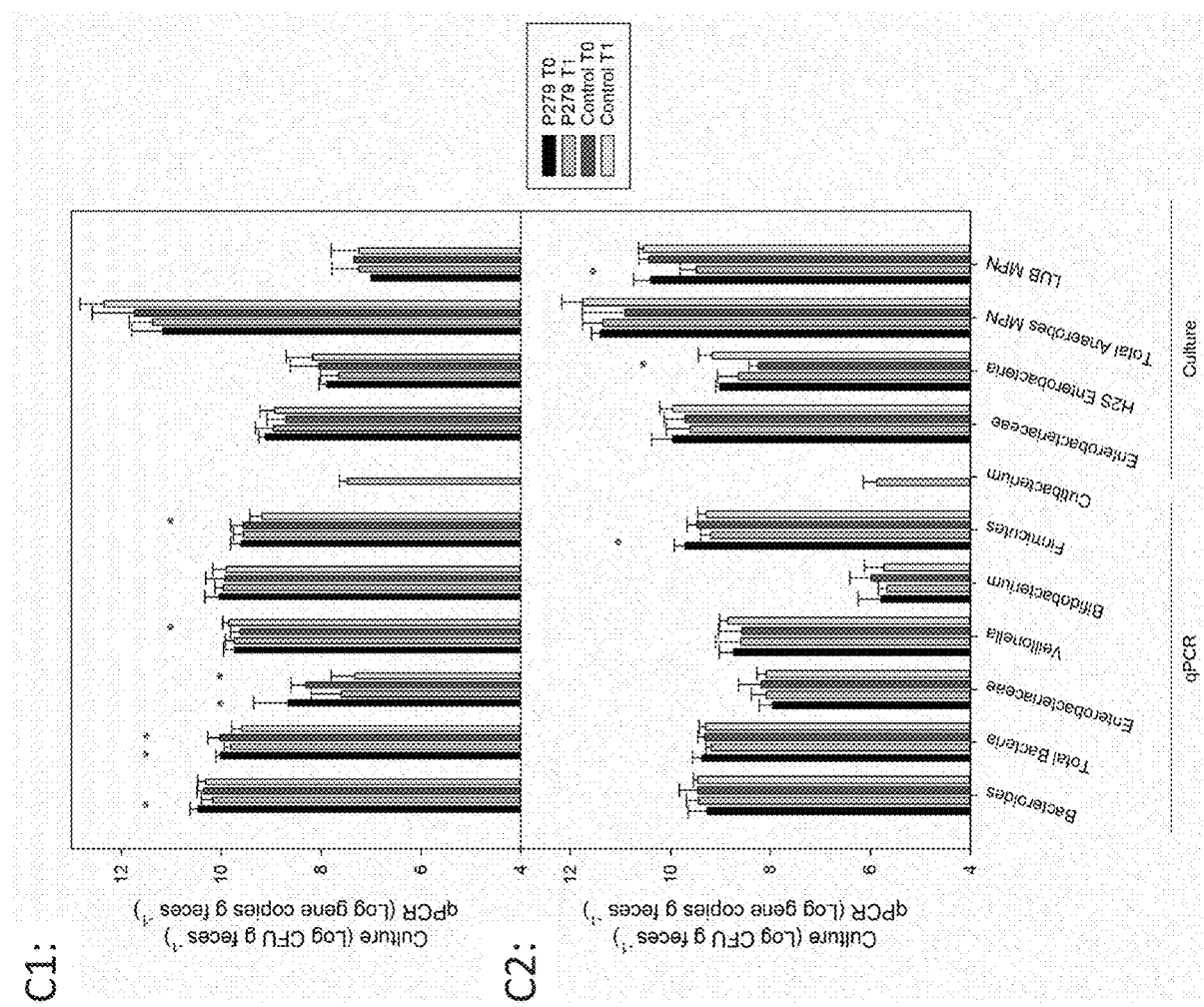
FIG. 7 depicts bar graphs of enumeration by qPCR and culture methods of main bacterial taxa at baseline and after intervention in rat feces after 10-day intervention for rats colonized with colicky fecal microbiota from colicky donors, according to Example 2 described herein.

FIG. 7 depicts bar graphs showing enumeration by qPCR and culture methods of main bacterial taxa at baseline and after intervention in rat feces after 10 day intervention: IMA rat study colonized with colicky fecal microbiota from donor C1 and C2; P279: rats receiving daily for 10 days $10^9$ CFU of *C. avidum* compare to non-supplemented control rats. Hydrogen excretion was significantly higher for IMA rats inoculated with feces from colicky donors than in rats inoculated with healthy donors.

Main bacterial taxa and non-SRB LUB community were enumerated on rat feces before and after intervention in the treatment and control groups. *Cutibacterium* were detected at high levels in rats of the treated group, supplemented with *C. avidum*. Viable cell numbers of *C. avidum* detected by plating of treated rat feces were Log 6.9±0.5 CFU g feces$^{-1}$ and Log 5.4±0.3 cells g feces$^{-1}$ for C1 and C2 rats, respectively. No significant changes were detected by 16S RNA sequencing (FIGS. 6A-B) and qPCR (FIG. 7A-B) in the bacterial profiles of fecal samples of treated rats were observed compared with baseline, and with control untreated rat groups. Our data show that *Cutibacterium* can colonize the gut of IMA rat, but did not affect the microbial profile of feces compare to control and treated rats before the intervention.

Figure 8:
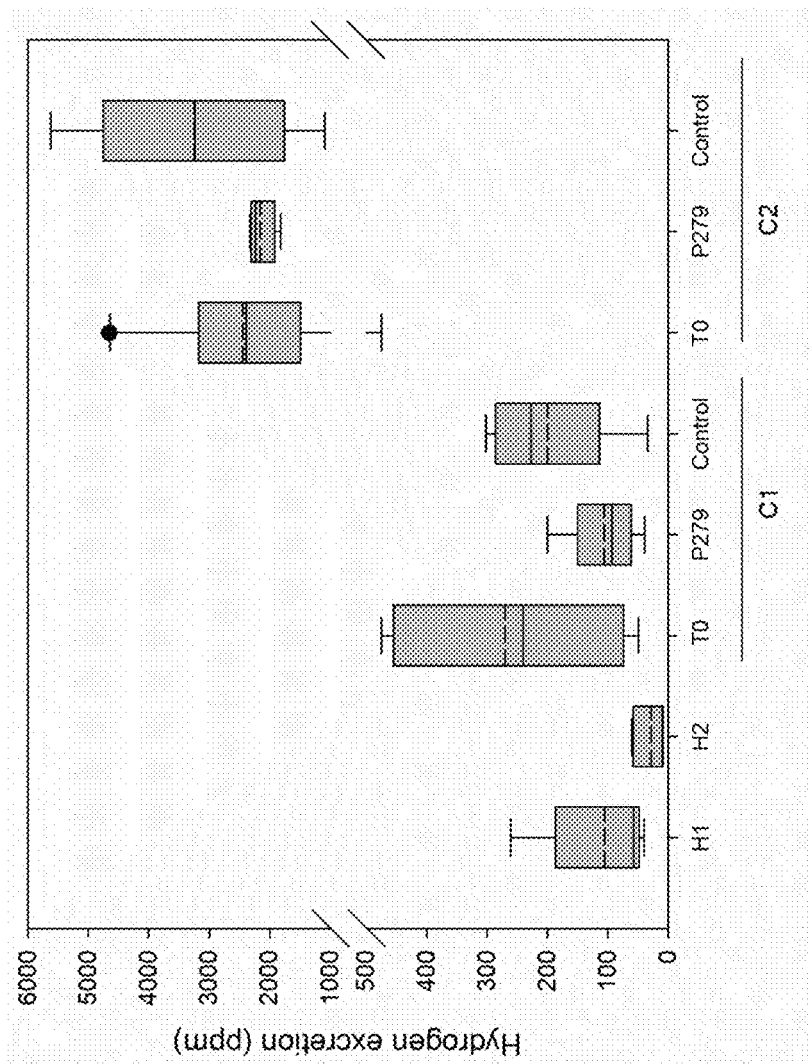
FIG. 8 is a bar graph showing the hydrogen produced by single IMA rat after 24 hour housing in respiratory chambers, according to Example 2 described herein.

FIG. 8 depicts a bar graph showing the hydrogen produced by single IMA rat after 24 h housing in respiratory chambers: IMA rat study colonized with healthy (H1 and H2) and colicky (C1 and C2) fecal microbiota; P279: rats receiving daily $10^9$ CFU of *C. avidum* compare to non-supplemented control rats. Hydrogen excretion was measured in IMA rats inoculated with feces from healthy (H1 and H2) and colicky (C1 and C2) donors at day 27. IMA rats inoculated with H1 and H2 excreted much lower levels of hydrogen (105±91 and 28±26 ppm for H1 and H2 IMA rats) than rats inoculated with C1 and C2 feces (270±192 and 2449±1293 ppm. After supplementation with *C. avidum* P279, while C1 IMA rats excreted significantly less $H_2$ (106.3±53.8 ppm; p 0.03) than rats of control group

TABLE 3

Table 3. Enumeration of main bacterial taxa by qPCR and MPN of total anaerobes in feces from donors and IMA rats.

| Donor | qPCR (Log 165 rRNA gene copies g feces$^{-1}$) | | | | | | | Culture results (Log CFU g feces$^{-1}$) |
|---|---|---|---|---|---|---|---|---|
| | Firmicutes | Bacteroides | *Veillonella* | *Bifidobacterium* | Enterobacteriaceae | *Propionibacterium* | Total Bacteria | Total bacteria MPN |
| H1 | 8.6 | 10.2 | 6.1 | 9.6 | 8.8 | BDL | 10.5 | 11.5 |
| H1 IMA rats | 9.8 ± 0.1 | 10.7 ± 0.1 | 9.8 ± 0.2 | 10.4 ± 0.2 | 9.0 ± 0.4 | 7.2 ± 0.5 | 11.0 ± 0.1 | 11.0 |
| H2 | 8.6 | 5.2 | 5 | 10.1 | 3.8 | BDL | 10.2 | 10.2 |
| H2 IMA rats | 9.5 ± 0.2 | 5.1 ± 0.3 | 3.8 ± 0.4 | 10.3 ± 0.2 | 9.0 ± 0.2 | BDL | 10.7 ± 0.2 | 10.7 |
| C1 | 9.0 | 8.2 | 4.6 | 8.9 | 8.0 | BDL | 9.0 | 10.0 |
| C1 IMA rats | 9.6 ± 0.2 | 10.4 ± 0.1 | 9.7 ± 0.2 | 10.0 ±0.3 | 8.5 ± 0.6 | BDL | 10.0 ± 0.1 | 11.5 ± 0.8 |
| C2 | 9.1 | 7.1 | 7.5 | 6.5 | 8.2 | BDL | 8.9 | 10.1 |
| C2 IMA rats | 9.6 ± 0.2 | 9.4 ± 0.4 | 8.6 ± 0.5 | 5.9 ± 0.4 | 8.1 ± 0.4 | BDL | 9.3 ± 0.2 | 11.0 ± 0.9 |

Acetate and propionate were the main SCFA in caecum supernatant as for the infant feces, and butyrate concentrations were low close to detection limit. The data are indicative of the validity of the IMA rat model for mimicking the gut microbiota of colicky infant.

(200±97.3 ppm). Moreover, this effect was confirmed by the second group of C2 IMA rats trial, where C2 IMA rats treated with *C. avidum* P279 excreted much less hydrogen than the control group (2152±229 and 248.0±1686.9 ppm H2, respectively). Our data demonstrate the beneficial effects of *C. avidum* supplementation, leading to decrease hydrogen excretion, as a cause of abdominal distention and pain in colic, compared to not-treated control groups.

Short chain fatty acid (SCFA) and metabolites in rat caecum content after sacrifice showed that formiate was significantly (p 0.01) lower in C1 IMA rats treated with *C. avidum* P279 (0.4±0.6 mM) than in control rats (1.7±1.2 mM). C2 IMA rats treatment group exhibited higher concentrations of acetate (11.9±2.9 mM; p<0.01) and propionate (7.2±3.3 mM; p 0.03) that are main metabolites of *Cutibacterium* in caecum supernatant than the control group (6.4±2.5 mM and 3.3±0.9 mM, respectively). Because acetate and propionate are produced by *Cutibacterium* at theoretical ratio of 3 to 2, the observed increase of these main fermentation metabolites in the treated group is consistent with the functional role of supplemented bacterium.

EXAMPLE 3

An example of the composition of an infant formula is given below. The individual process steps for manufacturing such an infant formula follow conventional manufacturing. The composition given in nutrient content per 100 kcal (per liter).

TABLE 4

| Component: | Nutrient Content, per 100 kcal (per liter) |
|---|---|
| Energy (kcal) | 100 (670) |
| Protein(g) * | 1.83 (12.3) |
| Fat (g) | 5.3 (35.7) |
| Linoleic acid (g) | 0.79 (5.3) |
| α-Linolenic acid (mg) | 101 (675) |
| Lactose (g) | 11.2 (74.7) |
| Prebiotic (90% GOS) (g) | 0.58 (3.9) |
| Prebiotic (10% FOS) (g) | 0.06 (0.4) |
| Minerals (g) ** | 0.37 (2.5) |
| Fe (mg) | 1.2 (8) |
| I (μg) | 15 (100) |
| Cu (mg) | 0.06 (0.4) |
| Zn (mg) | 0.75 (5) |
| Vitamin A*** (μg) | 105 (700) |
| Vitamin D (μg) | 1.5 (10) |
| Vitamin E ****(mg) | 0.8 (5.4) |
| Vitamin K (μg) | 8 (54) |
| Vitamin C (mg) | 10 (67) |
| Vitamin B1 (mg) | 0.07 (0.47) |
| Vitamin B2 (mg) | 0.15 (1.0) |
| Niacin (mg) | 1 (6.7) |
| Vitamin B6 (mg) | 0.075 (0.50) |
| Folic acid (μg) | 9 (60) |
| Pantothenic acid (mg) | 0.45 (3) |
| Vitamin B12 (μg) | 0.3 (2) |
| Biotin (μg) | 2.2 (15) |
| Choline (mg) | 10 (67) |
| *Cutibacterium avidum* | $2 \times 10^7$ cfu/g of powder |
| *Lactobacillus reuteri* | $2 \times 10^7$ cfu/g of powder |

* mixture of 60% MSWP28 and 40% casein
** Na (mg) 23 (150); K (mg) 89 (590) Cl (mg) 64 (430) Ca (mg) 62 (410) P (mg) 31 (210) Mg (mg) 7 (50) Mn (mg) 8 (50), Se (μg) 2 (13)
*** expressed as retinol equivalents RE
**** α-alpha-tocopherol equivalent TE

EXAMPLE 4

An example for *C. avidum* suspension for administration to an infant is given below. A combination of *C. avidum* and *L. reuteri* can also be administered:
(i) orally, directly to the infant (pure or diluted in water or mother's milk for example),
(ii) as a supplement (for example as a human milk fortifier supplement),
(iii) as a pharmaceutical composition, or
(iv) as a nutraceutical composition.

A suspension of *C. avidum* in oil is produced by mixing sterile oil (for example a mixture of 95% sunflower oil and 5% medium chain triglyceride oil of palm kernel) with a freeze-dried powder of the bacteria in order to obtain a final cell concentration of $2 \times 10^9$ cfu/g of suspension.

A suspension of *L. reuteri* in oil is produced by mixing sterile oil (for example a mixture of 95% sunflower oil and 5% medium chain triglyceride oil of palm kernel) with a freeze-dried powder of the bacteria in order to obtain a final cell concentration of $1 \times 10^9$ cfu/g of suspension.

The package includes a white desiccant device for prolongation of shelf-life.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

The invention claimed is:

1. A method of treating infantile colic in a subject in need thereof, the method comprising administering to the subject an infant nutritional product comprising:
   (a) viable lactic acid-producing bacteria from one or more live bacteria strains;
   (b) viable, lactate utilizing, propionic acid producing bacteria from one or more live *Cutibacteria* strains; and
   (c) optionally prebiotics.

2. The method according to claim 1, wherein said viable, lactate utilizing, propionic acid producing bacteria are *C. avidum*.

3. The method according to claim 1, wherein said viable lactic acid-producing bacteria (a) are selected from the group consisting of *Bifidobacterium* spp., *Lactobacillus* spp., *Lactococcus* spp., *Streptococcus* spp., *Enterococcus* spp., *Leuconostoc* spp., and *Weissella* spp.

4. The method according to claim 1, wherein the infant nutritional product further comprises additives.

5. The method according to claim 1, wherein the infant nutritional product includes probiotics, and the prebiotics are selected from the group consisting of fructooligosaccharides (FOS) and galactooligosaccharides (GOS).

6. The method according to claim 1, wherein the infant nutritional product further comprises baby milk or baby milk powder.

7. The method according to claim 1, wherein the amount of said viable bacteria is in the range of $10^2$ to $10^{12}$ CFU per gram or per mL of product.

8. The method according to claim 1, wherein the infant nutritional product is designed to be administered to infants or young children starting from the age of 6 months and provides complete nutrition to the infant or child.

9. The method according to claim 1, comprising administering a baby formula comprising the infant nutritional product.

10. The method according to claim 9, wherein the baby formula is in the form of a baby milk.

11. The method according to claim 9, wherein the baby formula is in the form of a kit of parts, wherein a first part comprises the infant nutritional product and the second part comprises a baby formula free of viable bacteria.

12. The method according to claim 11, wherein the second part comprises baby milk.

* * * * *